(12) United States Patent
Leblans et al.

(10) Patent No.: US 8,735,172 B2
(45) Date of Patent: May 27, 2014

(54) METHOD AND DEVICE FOR THE MANIPULATION OF MICROCARRIERS FOR AN IDENTIFICATION PURPOSE

(75) Inventors: Marc Jan René Leblans, Kontich (BE); Emmanuel Marie Paul Ernest Gustin, Vosselaar (BE); Christiaan Hubert Simon Roelant, Leuven (BE); Joseph Demeester, Ghent (BE); Stefaan Cornelis De Smedt, Mariakerke (BE); Kevin Braeckmans, Destelbergen (BE)

(73) Assignee: Biocartis S.A., Lausanne (CH)

( * ) Notice: Subject to any disclaimer, the term of this patent is extended or adjusted under 35 U.S.C. 154(b) by 0 days.

(21) Appl. No.: 12/888,187

(22) Filed: Sep. 22, 2010

(65) Prior Publication Data

US 2011/0082046 A1 Apr. 7, 2011

Related U.S. Application Data

(63) Continuation of application No. 10/399,921, filed as application No. PCT/EP01/12194 on Oct. 19, 2001.

(30) Foreign Application Priority Data

Oct. 19, 2000 (EP) .................................. 00203627

(51) Int. Cl.
*G01N 33/53* (2006.01)
*G01R 15/20* (2006.01)
*G01R 33/12* (2006.01)
*G01N 27/74* (2006.01)

(52) U.S. Cl.
CPC ................. *G01N 33/53* (2013.01); *G01R 15/20* (2013.01); *G01R 33/1269* (2013.01); *G01N 27/745* (2013.01)
USPC .......................................................... 436/518

(58) Field of Classification Search
None
See application file for complete search history.

(56) References Cited

U.S. PATENT DOCUMENTS 3,786,237 A 1/1974 Postal
4,053,433 A * 10/1977 Lee ............................ 252/408.1

(Continued)

FOREIGN PATENT DOCUMENTS

EP 1077177 2/2002
GB 2289150 A 11/1995

(Continued)

OTHER PUBLICATIONS

Webster's Third New International Dictionary of the English Language Unabridged, 1963, G & C Merriam Company, Springfield, MA, p. 1130.*

(Continued)

*Primary Examiner* — Chris L Chin
*Assistant Examiner* — Richard Moerschell
(74) *Attorney, Agent, or Firm* — Clark & Elbing LLP

(57) ABSTRACT

The present invention relates to a method for the manipulation for an identification purpose of a microcarrier comprising the steps of: (a) an identification purpose step of the microcarrier; and (b) a positioning and orientation step prior to or during the identification purpose step, wherein the identification purpose step is a detection step for the detection of an encoded microcarrier having an anisotropy in its shape. The invention further relates to an apparatus for the manipulation for identification purposes of a microcarrier comprising means for identification purposes such as a microscope and means for the positioning and orientation of the microcarriers.

21 Claims, 22 Drawing Sheets

(56) References Cited

U.S. PATENT DOCUMENTS

| | | | |
|---|---|---|---|
| 4,390,452 A | | 6/1983 | Stevens |
| 4,863,264 A | | 9/1989 | Miyake et al. |
| 4,909,992 A | * | 3/1990 | Bjorkman ............... 422/509 |
| 5,129,974 A | | 7/1992 | Aurenius |
| 5,329,090 A | | 7/1994 | Woelki et al. |
| 5,492,222 A | | 2/1996 | Weaver |
| 5,540,951 A | | 7/1996 | Nagayama et al. |
| 5,565,324 A | | 10/1996 | Still et al. |
| 5,635,347 A | | 6/1997 | Link et al. |
| 5,690,895 A | | 11/1997 | Matsumoto et al. |
| 5,705,402 A | | 1/1998 | Leland et al. |
| 5,721,099 A | | 2/1998 | Still et al. |
| 5,736,332 A | | 4/1998 | Mandecki |
| 5,751,629 A | | 5/1998 | Nova et al. |
| 5,770,459 A | | 6/1998 | Massey et al. |
| 5,779,976 A | | 7/1998 | Leland et al. |
| 5,789,172 A | | 8/1998 | Still et al. |
| 5,793,485 A | | 8/1998 | Gourley |
| 5,798,083 A | | 8/1998 | Massey |
| 5,876,593 A | * | 3/1999 | Liberti et al. ............ 210/95 |
| 5,888,370 A | | 3/1999 | Becker et al. |
| 5,891,354 A | * | 4/1999 | Lee et al. ............... 216/99 |
| 5,935,779 A | | 8/1999 | Massey et al. |
| 5,962,218 A | | 10/1999 | Leland et al. |
| 6,023,540 A | | 2/2000 | Walt et al. |
| 6,200,628 B1 | | 3/2001 | Rozumek et al. |
| 6,214,618 B1 | | 4/2001 | Hillegas et al. |
| 6,266,459 B1 | | 7/2001 | Walt et al. |
| 6,325,973 B1 | | 12/2001 | Leland et al. |
| 6,327,410 B1 | | 12/2001 | Walt et al. |
| 6,329,139 B1 | * | 12/2001 | Nova et al. ............... 506/30 |
| 6,350,620 B2 | | 2/2002 | Chang et al. |
| 6,458,165 B1 | | 10/2002 | Foucher et al. |
| 6,461,690 B2 | | 10/2002 | Corbett |
| 6,841,147 B2 | | 1/2005 | Zsebo et al. |
| 6,844,170 B1 | | 1/2005 | Moore et al. |
| 6,908,737 B2 | | 6/2005 | Ravkin et al. |
| 2002/0084329 A1 | | 7/2002 | Kaye et al. |
| 2004/0069857 A1 | | 4/2004 | Leblans et al. |
| 2006/0097056 A1 | | 5/2006 | De Smedt et al. |

FOREIGN PATENT DOCUMENTS

| | | | |
|---|---|---|---|
| JP | 62-032896 | | 2/1987 |
| WO | WO 93/16383 | | 8/1993 |
| WO | WO 95/29473 | | 11/1995 |
| WO | WO 98/40726 | * | 9/1998 ............ G01N 21/77 |
| WO | WO 98/53093 | | 11/1998 |
| WO | WO 99/18434 | | 4/1999 |
| WO | WO 99/19344 | | 4/1999 |
| WO | WO 99/19515 | | 4/1999 |
| WO | WO 99/24458 | | 5/1999 |
| WO | WO 99/37814 | | 7/1999 |
| WO | WO 99/60170 A1 | | 11/1999 |
| WO | WO 00/16893 | | 3/2000 |
| WO | WO 00/46595 | | 8/2000 |
| WO | WO 00/63695 | | 10/2000 |
| WO | WO 02/33419 | | 4/2002 |

OTHER PUBLICATIONS

Sakula (1982) Thorax 37:246.*

Giacomelli (2000) Magnetic Monopole Bibliography.*

U.S. Appl. No. 09/958,655, filed Jan. 9, 2002, De Smedt et al.

Berk et al., "Fluorescence Photobleaching with Spatial Fourier Analysis: Measurement of Diffusion in Light-Scattering Media," *Biophys. J.* 65:2428-2436 (1993).

Blonk et al., "Fluorescence Photobleaching Recovery in the Confocal Scanning Light Microscope," *Journal of Microscopy* 169:363-374 (1993).

Braeckmans et al., "Encoding Microcarriers: Present and Future Technologies," *Nature Reviews/Drug Discovery* 1(6):447-456 (2002).

Burgess, "Photobleaching Offers Coded Microspheres," *Photonics Spectra* [http://www.photonics.com/content/spectra/2003/May/tech/79798.aspx] (May 1, 2003).

De Smedt et al., "Diffusion of Macromolcules in Dextran Methacrylate Solutions and Gels as Studied by Confocal Scanning Laser Microscopy," *Macromolecules* 30:4863-4870 (1997).

De Smedt et al., "Structural Information on Hyaluronig Acid Solutions as Studied by Probe Diffusion Experiments," *Macromolecules* 27:141-146 (1994).

European Search Report for European Patent Application No. EP00203627, dated Apr. 5, 2001.

Gribbon et al., "Macromolecular Diffusion of Biological Polymers Measured by Confocal Fluorescence Recovery after Photobleaching," *Biophys. J.* 75:1032-1039 (1998).

International Search Report for International Patent Application No. PCT/EP01/12194, mailed Apr. 8, 2002.

Kaufman et al., "Measurement of Mass Transport and Reaction Parameters in Bulk Solution Using Photobleaching," *Biophys. J.* 60: 596-610 (1991).

Kubitscheck et al., "Single Nuclear Pores Visualized by Confocal Microscopy and Image Processing," *Biophys. J.* 70: 2067-2077 (1996).

Kubitscheck et al., "Two-Photon Scanning Microphotolysis for Three-Dimensional Data Storage and Biological Transport Measurements," *J. Microsc.* 182: 225-233 (1996).

Office Action mailed Jun. 12, 2006 in U.S. Appl. No. 11/319,153.
Office Action mailed Dec. 12, 2006 in U.S. Appl. No. 11/319,153.
Office Action mailed May 15, 2007 in U.S. Appl. No. 11/319,153.
Office Action mailed on Jan. 21, 2009 in U.S. Appl. No. 11/319,153.
Office Action mailed Jan. 28, 2003 in U.S. Appl. No. 09/958,655.
Office Action mailed Nov. 3, 2003 in U.S. Appl. No. 09/958,655.
Office Action mailed Apr. 25, 2006 in U.S. Appl. No. 09/958,655.
Office Action mailed Oct. 23, 2006 in U.S. Appl. No. 09/958,655.
Office Action mailed Oct. 31, 2007 in U.S. Appl. No. 09/958,655.
Office Action mailed Jul. 21, 2008 in U.S. Appl. No. 09/958,655.
Examiner's Answer to Appeal Brief mailed Jun. 29, 2010 in U.S. Appl. No. 09/958,665.
Office Action mailed Aug. 24, 2005, in U.S. Appl. No. 10/399,921.
Office Action mailed May 15, 2006, in U.S. Appl. No. 10/399,921.
Office Action mailed Feb. 6, 2007, in U.S. Appl. No. 10/399,921.
Office Action mailed Oct. 19, 2007, in U.S. Appl. No. 10/399,921.
Office Action mailed Feb. 22, 2008 in U.S. Appl. No. 10/399,921.
Office Action mailed Apr. 15, 2009 in U.S. Appl. No. 10/399,921.
Office Action mailed Jun. 23, 2010 in U.S. Appl. No. 10/399,921.

Peters and Scholz, "Fluorescence Photobleaching Techniques," *New Techniques of Optical Microscopy and Microspectroscopy* (Richard J. Cherry, ed.), pp. 199-228 (Chapter 8), CRC Press Inc.: Boca Raton, FL (1991).

Poitevin et al., "Study of the Translation Diffusion of Macromolecules in Beads of Gel Chromatography by the FRAP Method," *Biophysical Chemistry* 31:247-258 (1988).

Stenekes et al., "The Preparation of Dextran Microspheres in an All-Aqueous System: Effect of the Formulation Parameters on Particle Characteristics," *Pharmaceutical Research* 15(4):557-561 (1998).

Van Dijk-Wolthuis et al., "Reaction of Dextran with Glycidyl lylethacrylate: An Unexpected Transesterification," *Macromolecules* 30:3411-3413 (1997).

"Webster's Third New International Dictionary of the English Language Unabridged," G&C Merriam Company, Springfield, MA p. 1130 (1963).

Wedekind et al., "Line-Scanning Microphotolysis for Diffraction-Limited Measurements of Lateral Diffusion," *Biophys. J.* 71:1621-1632 (1996).

Wedekind et al., "Scanning Microphotolysis: A New Photobleaching Technique Based on Fast Intensity Modulation of a Scanned Laser Beam and Confocal Imaging," *J. Microsc.* 176:23-33 (1994).

* cited by examiner

| | | | | | | | | |
|---|---|---|---|---|---|---|---|---|
| A | | 0123 | L | | 0303 | W | | 1232 |
| B | | 0132 | M | | 0232 | X | | 1312 |
| C | | 0213 | N | | 0323 | Y | | 1313 |
| D | | 0212 | O | | 1032 | Z | | 1212 |
| E | | 0312 | P | | 1203 | ! | | 1023 |
| F | | 0313 | Q | | 1202 | ? | | 1323 |
| G | | 0102 | R | | 1302 | | | |
| H | | 0103 | S | | 1303 | | | |
| I | | 0202 | T | | 1012 | | | |
| J | | 0203 | U | | 1013 | | | |
| K | | 0302 | V | | 1213 | | | |

METHOD AND DEVICE FOR THE MANIPULATION OF MICROCARRIERS FOR AN IDENTIFICATION PURPOSE

CROSS-REFERENCE TO RELATED APPLICATIONS

This application is a continuation of, and claims priority from, U.S. patent application Ser. No. 10/399,921, filed Apr. 16, 2003, which is the U.S. National Phase of PCT/EP01/12194, filed Oct. 19, 2001, which claims benefit of European Patent Application No. 00203627.5, filed Oct. 19, 2000.

This invention relates to the manipulation of microcarriers for an identification purpose, and more specifically but not limited to the manipulation of microcarriers having codes written on them. An example of these microcarriers is described in the prior filed, and at the time of the priority not yet published patent application no. PCT/EP00/03280. Said application is hereby enclosed by reference. Any reference in this disclosure to codes written "on" the microcarriers includes codes written on the surface of the microcarriers as well as codes written at an internal depth of the microcarriers. Identification purposes are for example the reading or detection and the labeling or encoding of the microcarrier.

Drug discovery and drug screening in the chemical and biological arts commonly involve performing assays on very large numbers of compounds or molecules. These assays typically include screening chemical libraries for compounds of interest, screening for particular target molecules in test samples, and testing generally for chemical and biological interactions of interest between molecules. The assays described above often require carrying out thousands of individual chemical or biological reactions. For example, a drug discovery assay may involve testing thousands of compounds against a specific target analyte. Any compounds that are. observed to react, bind, or otherwise interact with the target analyte may hold promise for any number of utilities where the observed interaction is believed to be of significance.

A number of practical problems exist in the handling of the large number of individual interactions required in the assays described above. Perhaps the most significant problem is the necessity to label and track each reaction. For example, if a reaction of interest is observed in only one in a group of thousands of reactions, the researcher must be able to determine which one of the thousands of initial compounds or molecules produced that reaction.

One conventional method of tracking the identity of the reactions is by physically separating each reaction into an individual reaction vessel within a high-density array and maintaining a record of the identity of the individual reactants were used in each vessel. Thus, for example, when a reaction of interest is observed in a vessel labeled as number 5 of 1000, the researcher can refer to the record of reactants used in the vessels and will learn from the record of vessel 5 what specific reactants were present to lead to the reaction of interest. Examples of the high-density arrays referred to above are 384-, 864-, 1,536-, 3,456-, and 9,600-well microtiter plate containers, where each well of a microtiter plate constitutes a miniature reaction vessel. Miniaturized reaction wells are used because they conserve space, allow to increase speed and reduce the cost of reagents used in the assays.

The use of microliter plate containers in chemical and biological assays, however, carries a number of disadvantages. For example, the use of the plates requires carefully separating a very large number of discrete reaction vessels, rather than allowing for all reactions to take place freely, and often more conveniently, in one reaction vessel. Furthermore, the requirement that the reaction volumes be spatially separated carries with it a physical limitation to the size of microtiter plate used, and thus to the number of different reactions that may be carried out on the plate.

In light of the limitations described above in the use of microtiter plates, some attempts have been made to develop other means of tracking individual reactions in high-throughput assays. These methods have abandoned the concept of spatially separating the reactions, and instead track the individual reactions by other means. For example, methods have been developed to carry out high-throughput assays and reactions on microcarriers as supports. Each microcarrier may contain one particular ligand bound to its surface to act as a reactant, and the microcarrier can additionally contain a "code" that identifies the microcarrier and therefore identifies the particular ligand bound to its surface. These methods described above allow for "random processing," which means that thousands of uniquely coded microcarriers, each having a ligand bound to their surface, may all be mixed and subjected to an assay simultaneously. Those microcarriers that show a favorable reaction of interest between the attached ligand and target analyte may then have their code read, thereby leading to the identity of the ligand that produced the favorable reaction.

A main problem in the prior art is the random position of microcarriers for identification purposes and therefore lacking efficiency in the encoding and in the identification. Merely positioning a encoded microcarrier on a support is not sufficient for allowing an efficient encoding and identification. Several documents disclose a positioning on a solid support. The practice of random processing described above requires accurate encoding of each of the microcarriers separately, and requires accurate, reliable, and consistent identification of the codes. Because assays using random processing rely heavily on the coding of the microcarriers for their results, the quality of the assays depends largely on the reliability, readability, unique code, number of codes, precise dimension and readability of the codes on the microcarriers. Attempts to code microcarriers are still limited to differential coloring (Dye-Trak microspheres), fluorescent labeling (Fluorospheres; Nu-flow), so-called remotely programmable matrices with memories (IRORI; U.S. Pat. No. 5,751,629), detachable tags such as oligonucleotides and small peptides (U.S. Pat. Nos. 5,565,324; 5,721,099; 5,789,172), and solid phase particles that carry transponders (U.S. Pat. No. 5,736,332). WO 98/40726 describes a solid support being an optical fiber bundle sensor in which separate microspheres carrying different chemical functionalities may be optically coupled to discrete fibers or groups of fibers within the bundle. The functionalities are encoded on the separate microspheres using fluorescent dyes and then affixed to wells etched in the end of the bundle. The disclosures of the patents cited above are incorporated by reference herein.

The invention provides in a first aspect a method for the manipulation of microcarriers wherein an improved position and orientation is obtained. In its broadest scope, the invention provides a method for the manipulation for an identification purpose of a microcarrier comprising the steps of:

(a) an identification purpose step of the microcarrier; and (b) a positioning and orientation step prior to or during the identification purpose step.

Although this method requires both a positioning and an orientation step prior or during the identification purpose step, the invention surprisingly results in a better, more efficient and more reliable identification purpose step. A main reason is the lack of randomness in the degree of freedom of the position of the microcarrier.

The present invention is especially suitable for enabling the reading or writing of a code on a microcarrier, whereby the code is generated by a spatial modulation created inside the microcarrier or on its outer surface. This spatial modulation may be defined as a known arrangement of a finite number of distinct volume elements located inside or on the surface of the microcarrier. The known arrangement of distinct volume elements can be generated by (i) changing one or more properties of the material in an individual volume element, or (ii) by removing material from an individual volume element, or (iii) by depositing material on an individual volume element, or (iv) by leaving an individual volume element unchanged, or a combination of the above possibilities. This known arrangement for example, may be such that these volume elements lie on one or more dimensions such as on a line arrangement or in a plane. The main object of the invention is then to position and orient the microcarrier in reference to the writing instrument and the reading instrument, such that knowledge on the position and orientation of the microcarrier allows the writing instrument to generate the code by creating a known arrangement of a finite number of distinct volume elements, which code can subsequently be reliably resolved by the reading instrument using said knowledge on the position and orientation of the microcarrier on which the code is written. Resolving the code is performed by measuring the properties of those volume elements that together constitute the code which is located within the microcarrier or on the surface of the microcarrier. The orientation may be done with reference to one, two, or all three axes, depending on the symmetry of the arrangement of the volume elements. If this known arrangement is designed to be symmetric around one or more axes, the microcarrier does not need to be oriented with reference to rotation around these axes.

The present invention provides a method for the manipulation for an identification purpose of a microcarrier comprising the steps of (a) an identification purpose step of the microcarrier; and (b) a positioning and orientation step prior to or during the identification purpose step. According to an embodiment, the identification purpose step is a detection step for the detection of an identifiable or encoded microcarrier. According to another embodiment, the identification purpose step is a labeling step resulting in an identifiable or encoded microcarrier.

In another embodiment, the present invention provides a method for the manipulation for an identification purpose of a microcarrier, wherein said microcarrier is an encoded microcarrier encoded by a code written on the microcarrier. According to yet another embodiment, said microcarrier is encoded by a code written on the microcarrier by exposing the microcarrier to a high spatial resolution light source.

An embodiment of the method according to the invention is a method for the manipulation for identification purposes of a population of microcarriers, whereby the positioning and orientation step further comprises:
(b.1) the distribution of the population of microcarriers in a one-layer system; and
(b.2) restricting the rotational movement of the microcarriers.

Another embodiment according to the invention is a method, whereby the distribution of step b.1 results in a plane configuration having two dimensions (X,Y).

Another embodiment according to the invention is a method, wherein the distribution of step b.1 results in a line configuration. A one dimensional configuration results in a faster detection.

Another embodiment according to the invention is a method, wherein the distribution step is caused by transportation of the microcarriers preferably according to a laminar flow pattern in a liquid, gaseous or semi-solid environment. Transport of the microcarrier results in the possibility that the detection means can have a fixed position, thereby further improving the detection speed and dismissing any calibration of the detection means.

Another embodiment according to the invention is a method, wherein the laminar flow pattern in a liquid environment is provided in a capillary tube. Besides the laminar flow pattern, other flow patterns are possible.

Another embodiment according to the invention is a method, wherein the distribution step is caused by the positioning of the microcarriers in a semi-liquid or a liquid support, wherein said semi-liquid or liquid support may have a differential viscosity or density or can be composed of two or more semi-liquid or liquid layer with different viscosity or density. The microcarrier may then float or be positioned on or in the support at the interface of a viscosity or a density change. The position may vary according to the microcarrier density. The absence of a flow in said distribution of the microcarrier results in the possibility that the detection means could be mobile.

Another embodiment according to the invention is a method, whereby the positioning and orientation step results from a physical, mechanical, chemical or biological interaction on or near the microcarrier. As an example, chemical interaction can be any kind of interaction such as covalent or Vanderwaals interactions. A biological interaction can be obtained via a direct or indirect coupling of the microcarrier to a support or to a carrier realized via e.g. avidin/biotin, antibody/antigen, antibody/hapten, receptor/ligand, sugar/lectin, complementary nucleic acid (RNA or DNA, or combination thereof), enzyme/substrate, enzyme/cofactor, enzyme/inhibitor and/or immunoglobulin/ Staphylococcal protein A interaction.

Another embodiment according to the invention is a method, whereby the positioning and orientation step restricts the rotational movement of the microcarrier as a result of a magnetic field imposed on the microcarrier.

Another embodiment according to the invention is a method, whereby the positioning and orientation step restricts the rotational movement of the microcarrier as a result of an electrical field imposed on the microcarrier.

Another embodiment according to the invention is a method, whereby the positioning and orientation step results from the non-spherical configuration of the microcarrier, and more in particular by the ellipsoidal or cylindrical configuration of the microcarrier.

In a second aspect the invention relates to an apparatus for the manipulation for identification purposes of a microcarrier comprising means for reading or detection, or identification purposes such as optical means, electronic means, physical means, chemical means and magnetic means, or labeling means such as a high spatial resolution light source, and means for the positioning and orientation of the microcarriers.

In an embodiment, the invention relates to an apparatus for the manipulation for identification purposes of a microcarrier comprising means for identification purposes such as a microscope or labeling means such as a high spatial resolution light source, and means for the positioning and orientation of the microcarriers.

An embodiment according to the invention is an apparatus, whereby the means for positioning and orientation of the microcarriers comprises a solid support comprising a number of wells each suitable for housing at least one microcarrier and rotation restriction means.

An embodiment according to the invention is an apparatus, whereby the means for positioning and orientation of the microcarriers comprises a semi-liquid or a liquid support and rotation restriction means. According to another embodiment, said semi-liquid or liquid support may have a differential viscosity or density or can be composed of two or more semi-liquid or liquid layers with different viscosity or density. The microcarrier may then float or be positioned and oriented on or in the support at the interface of a viscosity or a density change. The position and orientation may vary according to the microcarrier density.

Another embodiment according to the invention is an apparatus, whereby the rotation restriction means are provided via a magnetic and/or electrical field.

Another embodiment according to the invention is an apparatus further comprising a reservoir suitable for containing a population of microcarriers, which reservoir is connectable to a capillary tube and pressure differential means for providing a laminar flow pattern in the capillary tube.

Another embodiment according to the invention is an apparatus, whereby further a magnetic and/or electrical field is provided for the restriction of the rotation of the microcarriers.

In a third aspect of the invention, a microcarrier is provided useful in the method of the first aspect which microcarrier is encoded by a code written on the microcarrier.

An embodiment according to the invention is a microcarrier, whereby the encoded microcarrier is characterized in that the code has been written by exposing the microcarrier to a high spatial resolution light source.

An embodiment according to the invention is a microcarrier, whereby the encoded microcarrier is characterized in that the code has been written by deposition of material on the surface or at the internal depth of said microcarrier.

Another embodiment according to the invention is a microcarrier further comprising a net electrical charge, an electrical dipole moment or a magnetic dipole moment. The microcarrier may also be ferro-, ferri- or paramagnetic as such, or has an anisotropy in its shape, an anisotropy in its mass distribution or any combination of these features.

Prior to discussing embodiments on how a microcarrier can be positioned and oriented in a certain way, it is necessary to describe the third aspect of the invention, i.e. the different types of microcarriers that can be used.

As used herein a "microcarrier" also termed "microsphere", "bead" or microparticle" relates to a reaction volume or a support which may be made from, for example, any materials that are routinely employed in high-throughput screening technology and diagnostics. For example, the microcarriers may be made from a solid, a semi-solid, or a combination of a solid and a semi-solid, and can be supports such as chemical and biological assays and syntheses. Non-limiting examples of these materials include cellulose, carboxymethyl cellulose, hydroxyethyl cellulose, agar, pore-glass, silica gel, polystyrene, brominated polystyrene, polyacrylic acid, polyacrylonitrile, polyamide, polyacrolein, polybutadiene, polycaprolactone, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly (lactide-co-glycolide), polyanhydride, polyorthoester, polyphosphazene, polyphosophaze, polysulfone, grafted copolymer such as polyethylene glycol/polystyrene, cross-linked dextrans, methylstyrene, polypropylene, acrylic polymer, paramagnetic, carbon, graphite, polycarbonate, polypeptide, hydrogels, liposomes, proteinaceous polymer, titanium dioxide, latex, resin, lipid, ceramic, charcoal, metal, bentonite, kaolinite, rubber, polyacrylamide, latex, silicone, e.g., polydimethyldiphenyl siloxane, dimethylacrylamide, and the like or combinations thereof are acceptable as well.

Preferred materials include latex, polystyrene, and cross-linked dextrans. The microcarriers may also be prokaryotic or eukaryotic cells or even some viruses. Said microcarriers may be of any shapes and sizes that should be suitable for encoding, positioning and orienting and further identification thereof. For example, the microcarriers may be in the form of spheres, or in the form of beads that are not necessarily spherical. The microcarriers may be, for example, cylindrical or oval. When spherical in shape, the microcarriers may have, for example, a diameter of 0.5 to 300 µm. The microcarrier may also have a diameter of 1 to 200 µm. Other examples of suitable sizes for said microcarrier could range from 10 to 90 um, The microcarrier can have a net electric charge or an electric dipole moment.

The microcarrier can be magnetic or have a magnetic dipole moment.

The microcarrier can have a certain anisotropy in its shape. For example, the microcarrier can have an axial symmetric shape, e.g, rod shaped, ellipsoidal or cylindrical.

The microcarrier can have a certain anisotropy in its mass distribution. For example, one region of the particle can be more dense so that one side is heavier than the other. Also, when a microcarrier has an asymmetric shape, this will be reflected by an asymmetric mass distribution as well.

The encoded microcarrier according to the teaching in PCTIEPOO/03280.

The microcarrier can be a combination of some or all of the above mentioned features.

The microcarrier may have different properties such as optical transparency, ferromagnetism, and can have functional surface group for binding ligands such as proteins. The microcarrier may also contain one or more dyes such as fluorophores, luminophores and the like, or a combination thereof. The ferromagnetism can be introduced by either in situ precipitation of ferromagnetic material or coating with a polymer containing ferromagnetic nanoparticles. Examples of ferromagnetic materials include but are not limited to $Cr_2O_3$, $Fe_2O_3$, $Fe_3O_4$, Ni- and Co-metals, other metal oxides and metals. The compounds can be introduced during the microcarrier preparation or in a post modification step such as soaking or coating. The ferromagnetic material can be present in said microcarrier at a concentration ranging from 0.1 to 50% by weight, or at a concentration ranging from 0.5 to 40%, or for example at a concentration ranging from 1 to 30%.

The codes written on the microcarriers according to the teaching in PCT/EP00/03280 may be of any geometry, design, or symbol that can be written and read on the microcarriers. For example, the codes may be written as numbers or letters, or as codes in the form of symbols, pictures, bar codes, ring codes, or three-dimensional codes. Ring codes are similar to bar codes, except that concentric circles are used rather than straight lines. A ring may contain, for example, the same information as one bar. The codes may be written on the surface of the microcarriers or at an internal depth of the microcarriers. For example, the codes may be written at an internal depth of the microcarriers, and more particularly in the center plane of the microcarriers. Depending on the shape of the microcarriers, the center plane may be a preferable location for writing the code because it may provide the largest surface area available for writing. Furthermore, for microcarriers having curved surfaces, it may be more advantageous to write the codes at an internal depth rather than on the curved surfaces. This is because it may often be more convenient to write and read the codes on a flat plane rather than on a curved surface.

The codes can be written on the microcarriers, for example, by using a high spatial resolution light source, such as a laser, a lamp, or a source that emits X-rays, α and β rays, ion beams, or any form of electromagnetic radiation. The codes can also be written on the microcarriers through photochroming or chemical etching. A convenient method for writing the codes is through the use of a high spatial resolution light source, and in particular a laser or a lamp in combination with a confocal microscope. The codes may also be written at an internal depth of the microcarrier by using the above-described methods.

The codes can also be written by deposition of material on or in said microcarrier. Examples of method of deposition include but are not limited to laser deposition and electrochemical deposition. Examples of material which can be used for said deposition include but is not limited to any organic compound or material; any inorganic compound or material; a particulate layer of material or a composite material; polymeric materials; crystalline or non-crystalline materials; amorphous materials or glasses; carbonaceous material such as, for example, graphite particles or carbon nanotubes; metallic material, such as, for example, gold, silver, copper, nickel, palladium, platinum, cobalt, rhodium, iridium; any metal chalcognide; metal oxide such as for example, cupric oxide, titanium dioxide; metal sulfide, metal selenide, metal telluride, metal alloy, metal nitride, metal phosphide, metal antimonide, semiconductor, semi-metal. Said material can be deposited in the form of particles such as micro or nanoparticles. For example, the particles are nano-particles, that is, typically, particles in the size range of 10 nm to 1000 nm.

Knowledge on the position and orientation of the microcarrier is essential to facilitate the writing and/or reading of the above written codes involves, in particular when these identification purpose steps are performed in a high throughput application.

Knowledge on position and orientation of the microcarrier will improve even more the identification purpose steps.

The microcarriers may contain a photosensitive substance. For example, the microcarrier may contain a bleachable substance, and the codes on the microcarriers may be in the form of bleached patterns within the bleachable portions of the microcarriers. The microcarriers may contain the bleachable substance either on the surface of the microcarrier or also within the body of the microcarrier. Any reference in this application to the bleaching of substances "on" the microcarriers includes bleaching at the surface of the microcarrier as well as bleaching at an internal depth of the microcarriers. Preferred bleachable substances include bleachable fluorescent or electromagnetic radiation absorbing substances. The microcarriers may contain bleachable luminophores. Examples of luminophores that can be used include fluorescers, phosphorescers, or scintillators. Bleachable chemiluminescent, bioluminescent, or colored substances may be used. Non-limiting examples of bleachable substances are listed herein: 3-Hydroxypyrene 5,8,10-Tri Sulfonic acid, 5-Hydroxy Tryptamine, 5-Hydroxy Tryptamine (5-HT), Acid Fuhsin, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocouniarin, Anthroyl Stearate, Aryl- or Heteroaryl-substituted Polyolefin, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy F1, BOPRO 1,Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH-CH3, DAPI, Diamino Phenyl Oxydiazole (DAO), Dimethylamino-5-Sulphonic acid, Dipyrrometheneboron Difluoride, Diphenyl Brilliant Flavine 7GFF, Dopamine, Eosin, Erythrosin ITC, Ethidium Bromide, Euchrysin, FIF (Formaldehyde Induced Fluorescence), Flazo Orange, Fluo 3, Fluorescamine, fluorescein isothiocyanate ("FITC"), Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Hoechst 33258, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nile Red, Nitrobenzoxadidole, N-(7-Nitrobenz-2-oxa-1,3-diazol-4-yl)diethyl amine (NODD). Noradrenaline, Nuclear Fast Red, Nuclear Yellow, Nylosan Brilliant Flavin E8G, Oregon Green, Oxazine, Oxazole, Oxadiazole, Pacific Blue, Pararosaniline (Feulgen), Phorwite AR Solution, Phorwite BKL, Phorwite Rev, Phorwite RPA, Phosphine 3R, Phthalocyanine, phycoerythrines, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarl 1, sulpho Rhodamine B Can C, Sulpho Rhodamine G Extra, Tetracycline, Texas Red, Thiazin Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, YO PRO 1, or combinations thereof. Optionally such bleachable substances will contain functional groups capable of forming a stable fluorescent product with functional groups typically found in biomolecules or polymers including activated esters, isothiocyanates, amines, hydrazines, halides, acids, azides, maleimides, alcohols, acrylamides, haloacetamides, phenols, thiols, acids, aldehydes and ketones. With regard to the volume of substance that may be bleached within the microcarriers, one example of such a volume is between 0.01 cubic nanometer and 0.01 cubic millimeter of the microcarrier, another example of such a volume is between 1 cubic nanometer and 100 000 cubic micrometer, yet another example of such a volume is between 10 000 and 10 000 cubic micrometer, another example of such a volume is between 0.01 cubic micrometer and 1000 cubic micrometer. The bleachable substances should be chosen so that, when bleaching occurs, the code remains on the microcarrier at least for the period of time that is desired for the use of the micro-carriers and any necessary reading of the codes. Said code should at least be preserved for the duration of the assay, wherein the microcarrier is used. This functional life of the code may be from several minutes up to several months, even up to several years depending on the assay to be performed. Thus, a certain amount of diffusion of non-bleached molecules into the bleached areas is acceptable as long as the useful life of the code is preserved. As used hereinafter the terms fluorescent dye, fluoresce; fluorochrome, or fluorophore are used interchangeably and bear equivalent meanings.

Codes bleached on microcarriers may also be written to have different intensities of fluorescence or color within bleached areas of the microcarriers. For example, a bleached coding may contain several different degrees of bleaching, thereby having several different intensities of fluorescence within the bleached region as a whole. Thus, microcarriers may be encoded not only by the geometry of the pattern bleached on the microcarriers, but also by the use of different fluorescent intensities within the pattern.

The codes may be written on the microcarriers through the use of scanning microphotolysis. ("SCAMP"). The technical features of SCAMP were first described in P. Wedekind et al., "Scanning microphotolysis: a new photobleaching technique based on fast intensity modulation of a scanned laser beam and confocal imaging," Journal of Microscopy, vol. 176, pp. 23-32 (1994), the content of which is incorporated by reference herein. Photobleaching is a well-known phenomenon referring to the fading of colors due to the fact that certain wavelengths of light when shone on a given pigment will cause the pigment's molecules to resonate and eventually break down. This is also the reason why fluorescent molecules often tend to bleach when excited by a powerful laser beam of specific wavelength. The codes may be photobleached using a conventional (non-scanning) light microscope, wherein a stationary (laser) light beam is focused on the sample during the bleaching process. The stationary position of the (laser) light beam during the bleaching process results in a photobleached area that has a circular geometry. Although non-scanning light microscopes technically yield an irradiated area of 2 µm or less in diameter, broadening of the bleach spot often occurs due to the stationary laser beam. This results in large circular bleached spots that are from one µm to 35 µm, typically from 10 µm to 20 µm in diameter or even larger such as 15 µm-35 µm. The availability of laser light scanning microscopes opened new opportunities for microphotolysis methods. The combination of photolysis, beam scanning, and confocal microscopy lead to the development of SCAMP. In SCAMP, bleaching occurs during scanning a sample by switching between low monitoring and high photobleaching laser intensity levels in less than a microsecond using an intensity modulation device such as an acousto-optical modulator ("AOM"). The combination of bleaching during scanning and the use of the AOM, which generates extremely short bleaching pulses, prevents the broadening of the bleach spot that occurs in conventional microphotolysis due to longer photobleaching times and the stationary laser beam. SCAMP allows for bleaching spots at the resolution limit of the objective lens used.

Writing codes on microcarriers may also involve bleaching the microcarriers to produce different levels of intensity in the bleached code. In addition to conveying the information in the design of the code itself, information can also be conveyed by different intensities within the bleached patterns. The ability to encode the microcarriers with different intensities may permit smaller codes on the microcarriers, thus saving space, but still conveying the same number or more of unique identifiers to code microcarriers. As an example, it is possible to bleach four different intensities in the beads. This can be accomplished in a number of ways, for example, by repeated bleaching over some portions of the bead relative to others, or by dissipating different levels of acoustic power into an AOM to produce a plurality of different laser powers that will create bleached patterns having different intensities based on the power of laser light used for each portion of the code.

The code may also be written by photochroming. Photochromic materials of interest undergo an irreversible change in light absorption that is induced by electromagnetic radiation, most common applications involve irreversible changes in color or transparency on exposure to visible or ultraviolet light. This is often seen as a change in the visible spectrum (400-700 nm), and can be rapid or very slow. A code could then be written in the inside of a bead that contains a photochromic dye, with focused UV light. There are two major classes of photochromic materials, inorganic and organic. Examples of the inorganic type are the silver halides. The organic photochromic systems can be subdivided according to the type of reaction. The photochromic compounds can be soluble in normal organic solvents such as hexane, toluene, acetone and DMSO. A non-limiting example is the use of a dispersion in polystyrene at concentration as high as 99%. Said compounds are also stable in low as well as high pH and are stable over a wide range of temperature. The photochromic compounds of interest are irreversible, wherein the color change is not reversed when the illumination is absent Most of the interesting compounds are thermally irreversible, i.e. they do not change back to the original colorless state at room temperature. Advantageous photochromic dyes are those that cannot be bleached back to their original state. Non-limiting examples of photochromic compounds of interest include derivatives of diarylethenes with heterocyclic aryl groups such as furan, indole, thiophene, selenophene, thiazole aryl groups, monomeric and polymeric forms of said compounds and the like. Examples of compounds include 1,2-dicyano-1, 2-bis (2,4,5-trimethylthiophen-3-yl)ethene, 2,3-bis (2,4,5-trimethylthiophen-3-yl) maleic anhydride, 1,2-bis (2,4-dimethyl-5-phenylthiophen-3-yl) perfluorocyclopentene, 1,2 bis (3-methyl-2-thienyl) perfluorocylopentene, 1,2-di(2-dimethyl-5-phenyl-thiophen-3-yl)perfluorocylopentene, 1,2-bis (2-methyl-3-thienyl)perfluorocyclopentene, 1,2-bis(2,5-dimethyl-3-thienyl) perfluorocyclopentene, 2-(1-octyl-2-methyl-3-indolyl)-3-(2,3,5-trimethyl-3-thienyl) maleic anhydride, 2-(2'-methoxybenzo[b]thiophen-3-yl)-3-(2-dimethyl-3-indolyl) maleic anhydride, 1,2-bis(2-methyl-5-phenyl-3-thienyl)-perfluoro cyclopentene, 1,2-bis(2,4-dimethyl-5-phenyl-3-thienyl)perfluoro cyclopentene, 1,2-bis (2-methyl-6-nitro-1-benzothiophen-3-yl)perfluorocyclopentene, 1,2-bis(2-methoxy-5-phenyl-3-thienyl) perfluorocyclopentene and the like. The photochromic compounds can be added to the microsphere in an amount ranging from 0.1 to 100%. In another embodiment, the photochromic compounds can be added to the microsphere in an amount ranging from 0.1 to 80%. In yet another embodiment, the photochromic compounds can be added to the microsphere in an amount ranging from 0.1 to 50%. The photochromic compound can also be added in an amount ranging from 1 to 3%. Photochroming is potentially faster and easier to control than the bleaching of fluorescent dye, because the coloration is normally linear with incident power. Readout is simplified because it is sufficient to take an image that reveals the code on a transparent background. A pattern written by localized bleaching in a fluorescent bead, on the other hand, would require a confocal microscope to detect it. It is possible to encode up to several tens of thousand microcarriers per second by photochroming.

Other methods for writing codes can also be used, such as code writing by changing the refractive index or by selective spectral photobleaching. In the case of spectral photobleaching the microcarriers may contain one or more different dyes each dye having unique spectral characteristics, and wherein one or more of these dyes may be bleached at different intensities.

Moreover, the microcarriers may be functionalized, i.e. said microcarrier may contain one or more ligands or functional units bound to the surface of the microcarriers. A large spectrum of chemical and biological functionalities may be attached as ligands to said microcarriers. These functionalities include all functionalities that are routinely used in high-throughput screening technology and diagnostics. The choice of the ligand will vary according to the analytes to target. The ligand may for instance be an organic entity, such as a single molecule or an assemblage of molecules. Examples of functionalization include the attachment, often via a linker, to an antibody or antibody fragment, to an oligonucleotide or a to a detectable tag. In some embodiments, the microcarrier can have multiple functionalities. As used herein, the term functional unit is meant to define any species that modifies, attaches to, appends from, coats or is covalently or non-covalently bound to the surface of said microcarrier. Functionalized, as defined herein, includes any modification of the surface of the microcarrier as covalently or non-covalently modified, derivatized, or otherwise coated with an organic, inorganic, organometallic or composition monolayer, multilayer, film, polymer, glass, ceramic, metal, semi-metal, semiconductor, metal oxide, metal chalcoginide, or combinations thereof. While such functionalization may occur most commonly at the outer surface of the microcarrier, it also may occur at interior surfaces of the microcarrier, as it might in the case in a porous or hollow microcarrier. Examples of target analytes for the microcarrier-bound ligands include antigens, antibodies, receptors, haptens, enzymes, proteins, peptides, nucleic acids, drugs, hormones, pathogens, toxins, or any other chemicals or molecules of interest. The ligands or functional units may be attached to the microcarriers by means conventionally used for attaching ligands to microcarriers in general, including by means of a covalent bound and through direct attachment or attachment through a linker. Furthermore, the microcarriers can be further functionalized in a variety of ways to allow attachment of an initial reactant with inorganic or organic functional group, including but not limited to, acids, amines, thiols, ethers, esters, thioesters, thioethers, carbamates, amides, thiocarbonates, dithiocarbonates, imines, alkenes, alkanes, alkynes, aromatic groups, alcohols, heterocycles, cyanates, isocyanates, nitriles, isonitriles, isothiocyanates, and organocyanides, or combinations thereof; any inorganic coordination complex, including but not limited to 2-, 3-, 4-, 5-, 6-, 7-, 8- and 9-coordinate complexes; any organometallic complex, including but not limited to species containing one or more metal-carbon, metal-silicon, or metal nitrogen bonds.

In another embodiment, the functional unit or functionalization of the microcarrier comprises a detachable tag. A detachable tag is any species that can be used for detection, identification, enumeration, tracking, location, positional triangulation, and/or quantitation. Such measurements can be accomplished based on absorption, emission, generation and/or scattering of one or more photons; absorption, emission generation and/or scattering of one or more particles; mass; charge; faradaic or non-faradaic electrochemical properties; electron affinity; proton affinity, neutron affinity; or any other physical or chemical property, including but not limited to solubility, polarizability, melting point, boiling point, triple point, dipole moment, magnetic moment, size, shape, acidity, basicity, isoelectric point, diffusion coefficient, or sedimentary coefficient. Such molecular tag could be detected or identified via one or any combination of such properties.

The present invention further relates to a method for the manipulation for an identification purpose of a microcarrier, comprising the steps of
a) positioning and orienting said microcarrier and
b) encoding said microcarrier by writing a code thereon,
c) allowing a target-analyte reaction on or in said microcarrier,
d) positioning and orienting said microcarrier, and
e) identifying said microcarrier,
whereby step (c) may also preceed step a).

Said method may conveniently also include a step whereby selectively those microcarriers are identified on which a target-analyte reaction of particular interest occurred. For instance, microcarriers with a target-analyte reaction of interest may be separated from the rest of the microcarriers, and those microcarriers may then be subjected to steps d) and e) of the above method.

According to another embodiment the present invention relates to a method, wherein the positioning and orientation step results from a physical, mechanical, chemical or biological interaction on or near said microcarrier. Another embodiment according to the invention is a method, whereby the positioning and orientation step restricts the rotational movement of the microcarrier as a result of a magnetic field imposed on the microcarrier. Another embodiment according to the invention is a method, whereby the positioning and orientation step restricts the rotational movement of the microcarrier as a result of an electrical or a magnetic field imposed on the microcarrier. Another embodiment according to the invention is a method, whereby the positioning and orientation step results from the non-spherical configuration of the microcarrier, and more in particular by the ellipsoidal or cylindrical configuration of the microcarrier. Another embodiment according to the invention is a method, whereby the positioning and orientation step results from the anisotropy in the mass distribution of the microcarrier. In such a case, an axial positioning and orientation in a gravitational as well as in a centrifugal manner may be obtained. Another embodiment according to the invention is a method, whereby the positioning and orientation step results from one or more combination of the above-described features. For example, a combination of magnetic forces and anisotropy in shape, combination of magnetic forces and anisotropy in weight, etc.

According to another embodiment, the positioning and orientation step can occur in a flow cell in a flow cytometer. The term flow cytometer is used herein for any apparatus that creates a single file flow of particles within a fluid and measures fluorescence from the particles. The sample fluid can be constrained within a narrow flow channel or by hydrodynamic focussing within a sheath fluid. For example, to position and orient particles in the flow, it is possible to employ the principle of hydrodynamic focusing in a so-called sheath flow cell or chamber. The sample fluid containing the particles can be injected into the center of a faster surrounding flow, the sheath flow, in front of a convergent nozzle. As the liquid passes through the convergence into the observation area, the sample flow is accelerated, stretched out and centered to pass through the focus of the observation system. The fluid may be air, water, solvent, buffer and the like. Different type of flow cells can be used, non-limiting examples are cited herein: cells with a closed optical chamber which can be used to detect fluorescence, scattering or light extinction, particles sorters using open-ended flow cells that divide the flow into electrically charged droplets, which can be deflected by an electrical field into containers to sort particles according to their fluorescent signal for example, flow cells that can have asymmetric nozzles or have asymmetric constrictions in the flow chamber to orient non-spherical particles onto the optical axis. Another example includes a flow cell apparatus as described in U.S. Pat. No. 5,690,895 incorporated herein by reference.

According to another embodiment, the positioning and orientation step may also occur by the dielectrophoretic caging of microcarriers. Dielectric particles, such as polystyrene microcarrier, suspended in a liquid can be manipulated by a high-frequency electrical field in a microelectrode cage. For example, microcarrier may be brought into a specially designed flow cell with a number of electrodes; by modifying the amplitude, frequency and phase of the fields, the microcarrier can be positioned and oriented.

According to another embodiment, the positioning and orienting of the microcarriers may also occur in a semi-liquid or a liquid support, wherein said semi-liquid or liquid support may have a differential viscosity or density or can be composed of two or more semi-liquid or liquid layer with different viscosity or density. The microcarrier may then float or be positioned on or in the support at the interface of a viscosity change. The position and orientation may vary according to the microcarrier density. The absence of a flow in said distribution of the microcarrier results in the possibility that the detection means could be mobile.

According to another embodiment, the positioning and orientation step may also occur by for example: trapping the microcarrier in strongly focused laser beams, so-called "laser tweezers". The positioning and orientation step may also occur using acoustic waves such as ultrasonic trapping, wherein the microcarrier is trapped in standing waves in a liquid. A "microlathe" which is usually used to modify the shape of particles with a UV laser, can also be used to position and orient the microcarrier for the identification step.

According to another embodiment, the positioning and orientation step may also occur using two or more combination of the above-described method for positioning and orienting.

According to an embodiment, the encoding step can be performed as described above in the description of the microcarrier. The encoding process, thus, can be selected from the group comprising photochroming, chemical etching, material deposition, photobleaching, or exposing said microcarrier to a high spatial resolution light source, such as a UV laser. According to another embodiment, the encoding step is performed by photochroming. According to another embodiment, the encoding step is performed by photobleaching.

According to an embodiment, the encoding comprises the writing of a code on a microcarrier whereby the code is generated by spatial modulation created inside the microcarrier or on its outer surface. According to yet another embodiment, said spatial modulation is a known arrangement of a finite number of distinct volume elements located inside or on the surface of the microcarrier. According to another embodiment, said spatial modulation can be generated by one or more steps comprising (i) changing one or more properties of the material in an individual volume element, (ii) removing material from an individual volume element, (iii) depositing material on an individual volume element or (iv) leaving an individual volume element unchanged, or a combination thereof.

According to an embodiment, the target analyte reaction step can consist of contacting a solution that may contain said analyte with a composition comprising a molecule, species or material that interacts with said analyte bound to an encoded microcarrier or a microcarrier and in the identification step further detecting whether an interaction has occurred. Said step also includes allowing a target analyte reaction for analytes in gas, vapor, semi-liquid or solid phase.

According to another embodiment, the present invention relates to a method wherein the identification step is performed by any physical or chemical means of interrogation, including but not limited to electromagnetic, magnetic, optical, spectrometric, spectroscopic and mechanical means. The identification step relates to the interpretation of the information coded within a microcarrier and may also be referred a as "interrogation step" or "reading step" or "differentiation step". The identification step may be performed using identification means including but not limited to visual inspection means, digital (CCD) cameras, video cameras, photographic film, or current instrumentation such as laser scanning devices, fluorometers, luminometers, photodiodes, quantum counters, plate readers, epifluorescence microscopes, scanning microscopes, confocal microscopes, capillary electrophoresis detectors, or by other means for amplifying the signal such as a photomultiplier tube or other light detector capable of detecting the presence, location, intensity, excitation and emission spectra, fluorescence polarization, fluorescence lifetime, and other physical properties of the fluorescent signal.

In another embodiment, the identification step is performed using an optical identification mean. The reading of the codes may be performed with an ordinary microscope if the code is on the surface of the microcarrier or, if the microcarrier is sufficiently translucent, at an internal depth of the microcarrier. Reading of the codes may also be performed using a confocal microscope, a transmission microscope or a fluorescence microscope. In particular, the codes may be read by suspending the microcarriers in an aqueous environment, placing the microcarriers between two glass slides or placing them in microcapillaries, and observing the codes through a microscope or confocal microscope. The reading may also be performed by using a laser beam scanning instrument. The reading may also be performed in a flow cell. A myriad of light sources and photodetectors are known in the flow cytometer art.

According to another embodiment, during the identification step, the microcarrier can be 3D-positioned in individual wells, in such a way that all microcarrier successively pass the stationary scanning beam of an identification mean. The reading velocity could also be increased if the microcarriers themselves pass the scan beam. The limiting factors in such a case would be the response time of the detector and the time required by the decoding algorithm. For examples, the wells could be positioned on a disc according to a spiral with a linear increasing radius. Therefore, the disc would merely need to rotate with a constant angular velocity during which the scanner moves with a constant velocity in a radial direction and the microcarriers will pass one by one the scan beam.

Said method can be useful for performing a target analyte assay. Example of target-analyte assay include but are not limited to DNA hybridization, enzyme-based assays, immunoassays, combinatorial chemistry assays, assays conducted to screen for certain compounds in samples, and also assay for detecting and isolating compounds from those samples.

The present invention further relates to a method for encoding a microcarrier, wherein the encoding comprises the writing of a code on a microcarrier whereby the code is generated by spatial modulation created inside the microcarrier or on its outer surface. According to an embodiment, the spatial modulation is a known arrangement of a finite number of distinct volume elements located inside or on the surface of the microcarrier. According to another embodiment, said spatial modulation is a known arrangement of a finite number of distinct volume elements located inside or on the surface of the microcarrier. According to yet another embodiment, said spatial modulation can be generated by one or more steps comprising (i) changing one or more properties of the material in an individual volume element, (ii) removing material from an individual volume element, (iii) depositing material on an individual volume element or (iv) leaving an individual volume element unchanged, or a combination thereof.

The present invention further relates to an encoded microcarrier obtainable by the method above described method, wherein the code on said encoded microcarrier is generated by spatial modulation created inside the microcarrier or on its outer surface. According to an embodiment, the spatial modulation is a known arrangement of a finite number of distinct volume elements located inside or on the surface of the microcarrier. According to another embodiment, said spatial modulation is a known arrangement of a finite number of distinct volume elements located inside or on the surface of the microcarrier. According to yet another embodiment, said spatial modulation can be generated by one or more steps comprising (i) changing one or more properties of the material in an individual volume element, (ii) removing material from an individual volume element, (iii) depositing material on an individual volume element or (iv) leaving an individual volume element unchanged, or a combination thereof.

The present invention further relates to the use of a microcarrier as described herein in a high-throughput screening assay. The assay may consist for example of detecting the presence or absence of one or more target analytes in a sample. Said assay may comprise contacting a microcarrier-bound ligand with at least one analyte, detecting whether the analyte has reacted or bound to the ligand, and reading the code of any microcarrier upon which any reaction or binding has occurred. Said assay may comprise choosing one or more ligands which bind or react with the one or more analytes, binding the ligands to a plurality of microcarriers, correlating the identity of the ligands with the codes on the microcarriers to which the ligands are bound, contacting the one or more analytes with the ligand-bound microcarriers, observing any microcarriers upon which the analyte has bound or reacted with the microcarrier-bound ligand, and reading the codes on the microcarriers to identify any ligands with which the one or more analytes have reacted, thereby determining the presence or absence of the one or more analytes. Said high-throughput screening assay using the encoded microcarriers can be carried out in water, in solvent, in buffer or in any biological fluid, including separated or unfiltered biological fluids such as urine, cerebrospinal fluid, pleural fluid, synovial fluid, peritoneal fluid, amniotic fluid, gastric fluid, blood, serum, plasma, lymph fluid, interstitial fluid, tissue homogenate, cell extracts, saliva, sputum, stool, physiological secretions, tears, mucus, sweat, milk, semen, vaginal secretions, fluid from ulcers and other surface eruptions, blisters, and abscesses, and extracts of tissues including biopsies of normal, malignant, and suspect tissues or any other constituents of the body which may contain the analyte of interest. Other similar specimens such as cell or tissue culture or culture broth are also of interest. Alternatively, the sample is obtained from an environmental source such as soil, water, or air; or from an industrial source such as taken from a waste stream, a water source, a supply line, or a production lot. Industrial sources also include fermentation media, such as from a biological reactor or food fermentation process such as brewing; or foodstuff, such as meat, game, produce, or dairy products.

The test sample can be pre-treated prior to use, such as preparing plasma from blood, diluting viscous fluids, or the like; methods of treatment can involve filtration, distillation, concentration, inactivation of interfering compounds, and the addition of reagents.

The present invention further encompasses a report comprising information obtained from the high-throughput assays described above.

The present invention further relates to a method for the preparation of an encoded microcarrier as described above comprising the step of writing a code on said microcarrier. Examples of processes for writing said codes include photochroming, chemical etching, material deposition, photobleaching, or exposing said microcarrier to a high spatial resolution light source. According to an embodiment, said code is written by photochroming. According to another embodiment, said code is written by photobleaching.

According to another aspect, the present invention relates to a computer for monitoring a high-throughput target-analyte assay with a microcarrier as described herein, wherein said computer is linked to an apparatus as described above.

According to an embodiment the present invention further relates to a device for high-throughput target-analyte assay, comprising a computer for monitoring said assay and an apparatus as described above. The device may comprise a microarray and an identification mean. Examples of identification means include but are not limited to optical means, electronic means, physical means, chemical means and magnetic means. The microarray will normally involve a plurality of different components. In theory there need by only one component, but there may be as many as $10^5$. While the number of components will usually not exceed $10^5$, the number of individual encoded microcarriers used may be substantially larger.

The encoded microcarriers in the microarray may be arranged in tracks. Headers can be provided for defining sites, so that particular interactions can be rapidly detected. Particularly, disks having circular tracks with headers defining sites on the tracks, so that positive signals can be interpreted in relation to the information provided by the header. The circular tracks are preferably concentric and may have a cross-section in the range of 5 to 5000 μm, or for example in the range of 100 to 1000 μm or from 500 to 2000 μm. Various modifications are possible, such as pre-prepared segments that may then be attached to the disk for assaying.

The above and other objects, features and advantages of the present invention will be more readily understood from the following description when taken in conjunction with the accompanying drawing, in which FIGS. 1-3 are cross-sectional views.

In FIG. 1 a spherical micro carrier is shown with a magnetic dipole moment coming from magnetic material inside. The magnetic field caused by the coils holds the microcarrier into place and orients it at the same time. When the magnetic material is placed outside the center of the microcarrier as is illustrated, a complete 3D-orientation is obtained because of the gravitation and the magnetic attraction.

In FIG. 2 spherical microcarriers are shown with a magnetic dipole moment transported by a fluid flowing through a capillary with velocity v. Two coils are provided that can induce a magnetic field parallel to the capillary. Outside the magnetic field, the carriers will rotate because of the friction of the fluid. Inside the coils, the magnetic field will try to align the dipole moment antiparallel to itself. thus eliminating the rotation in the direction of the movement of the particle.

In FIG. 3 a schematic representation is shown of the capillary system used to examine the positioning of microcarriers transported by a laminar flow inside a capillary using a confocal microscope.

FIG. 4 shows a confocal image with one particle flowing inside the capillary. The arrow at the right indicates the inside dimension of the capillary: 80 μm. The capillary and the water are completely dark since they do not emit fluorescent light. The field of view is 0.92 mm×0.10 mm. One particle is seen as a set of three separate lines rather than an actual disk because of the velocity of the particles and the particular way a confocal image is taken.

Since FIG. 4 is one of the pictures of a complete time series, the particle of FIG. 4 can indeed be found in FIG. 5 at the same position since it is the addition of all the pictures from the time series into one picture. From FIG. 5 it becomes clear that the particles indeed have a certain position when being transported by a laminar flow through the capillary (Pressure about 0.05 atm, wherein about as cited herein refers to plus or minus 15%). The particles follow one straight line at a constant distance from the capillary wall (the line seems to be tilted but that's because the capillary itself was positioned that way in the field of view).

FIG. 5 shows a composite picture of all the individual pictures of one time series, wherein all the particles that have passed in that time interval (pressure about 0.05 atm) are shown. It is clear that the particles all move along one straight line at a constant distance from the wall (but not in the center) of the capillary.

FIGS. 6 and 7 also show a composite picture from two different time series. FIG. 6 shows a composite picture with the same positioning at a higher pressure (about 0.1 atm). FIG. 7 shows a composite picture with the same positioning at a higher pressure (about 0.15 atm). The only difference between FIGS. 5, 6 and 7 is the applied pressure (about 0.05, 0.1 and 0.15 atm respectively), and thus the fluid velocity. The positioning is therefore valid at higher pressures as well.

Figure 16:
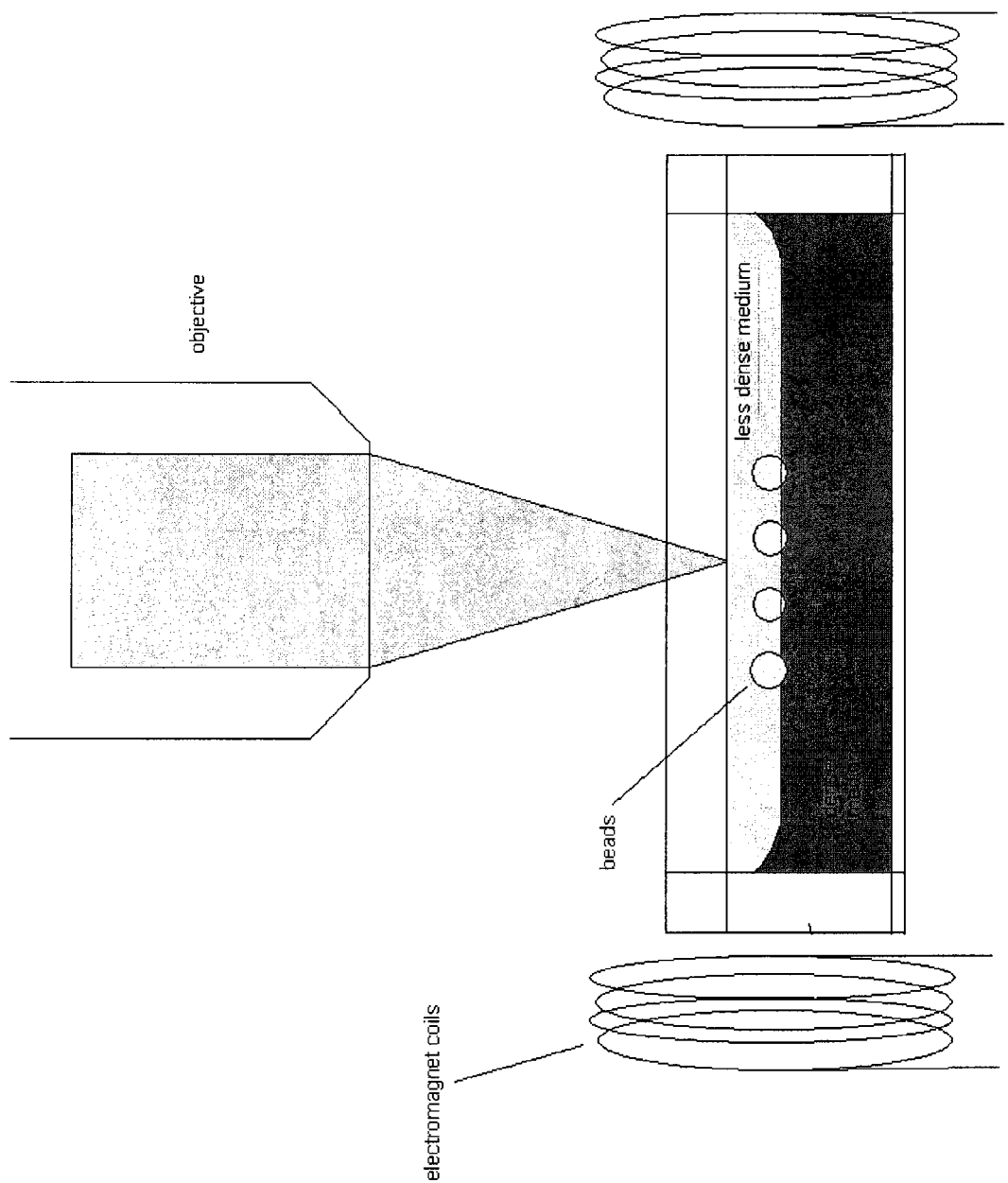

FIG. 16 shows a schematic representation of ferro-magnetic microcarriers in a support consisting of two liquids or semi-liquid of different density. Two coils are provided that can induce a magnetic field. Inside the coils, the magnetic field will try to align the dipole moment antiparallel to itself, thus positioning and orienting the microcarrier in a specific manner.

Figure 17:
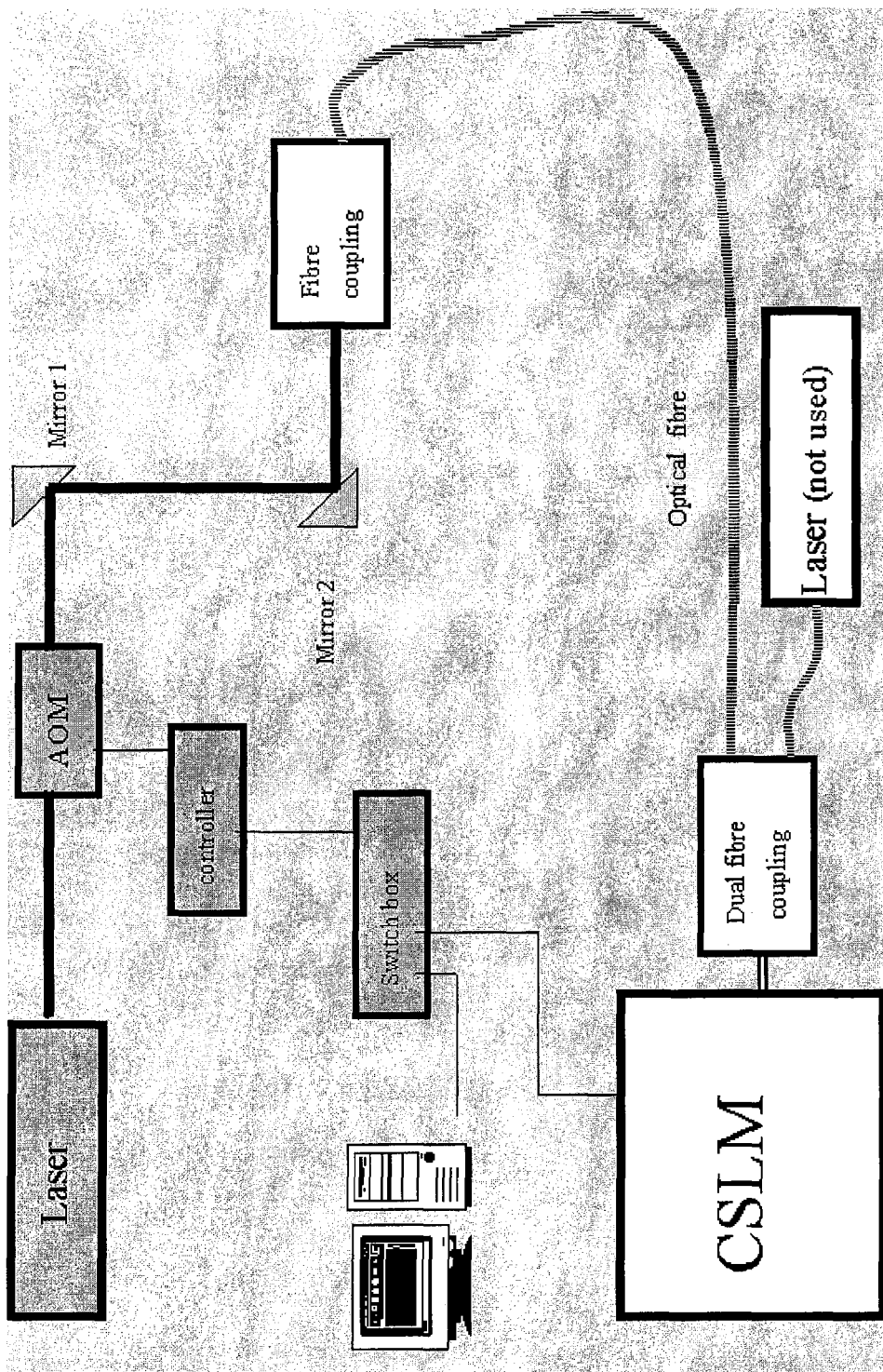

FIG. 17 shows a schematic representation of device comprising a Confocal Laser Scanning Microscope (CLSM) coupled to a powerful laser combined with a fast optical switch. The light source used is a Spectra Physics Stabilite 2017 Ar ion laser, tuned at a single wavelength, e.g. 488 nm. The AOM causes the laser light to be diffracted into multiple beams. The first order beam is then coupled to an optical fiber. The AOM is controlled by a PC and dedicated software to switch the intensity of the first order beam between two levels: a weak imaging beam and a strong bleaching beam. The fiber end is coupled into a 'dual fiber coupling' so that the light coming out of the fiber can be combined with the light from another laser (but is not used in the bleaching experiments). Finally the light enters the confocal scanning laser microscope (CSLM) and is focused on the sample. A bleaching pattern can be designed in dedicated software. While taking an image, which is done by scanning the laser light in a raster pattern, dedicated software controls the optical switch in such a way that low and high power laser light reaches the sample according to the designed pattern.

Figure 18:
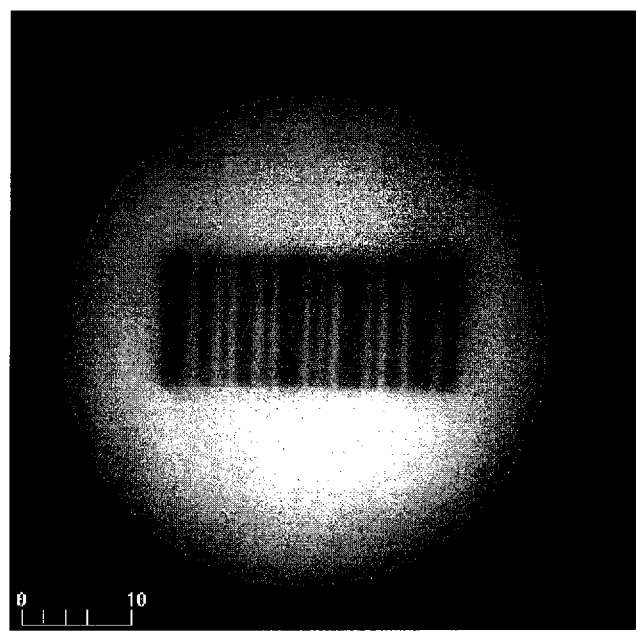

FIG. 18 shows a confocal image of a bleached barcode, using three widths and two intensity levels, in the central plane of a 45 micron polystyrene fluorescent microsphere.

Figure 19:
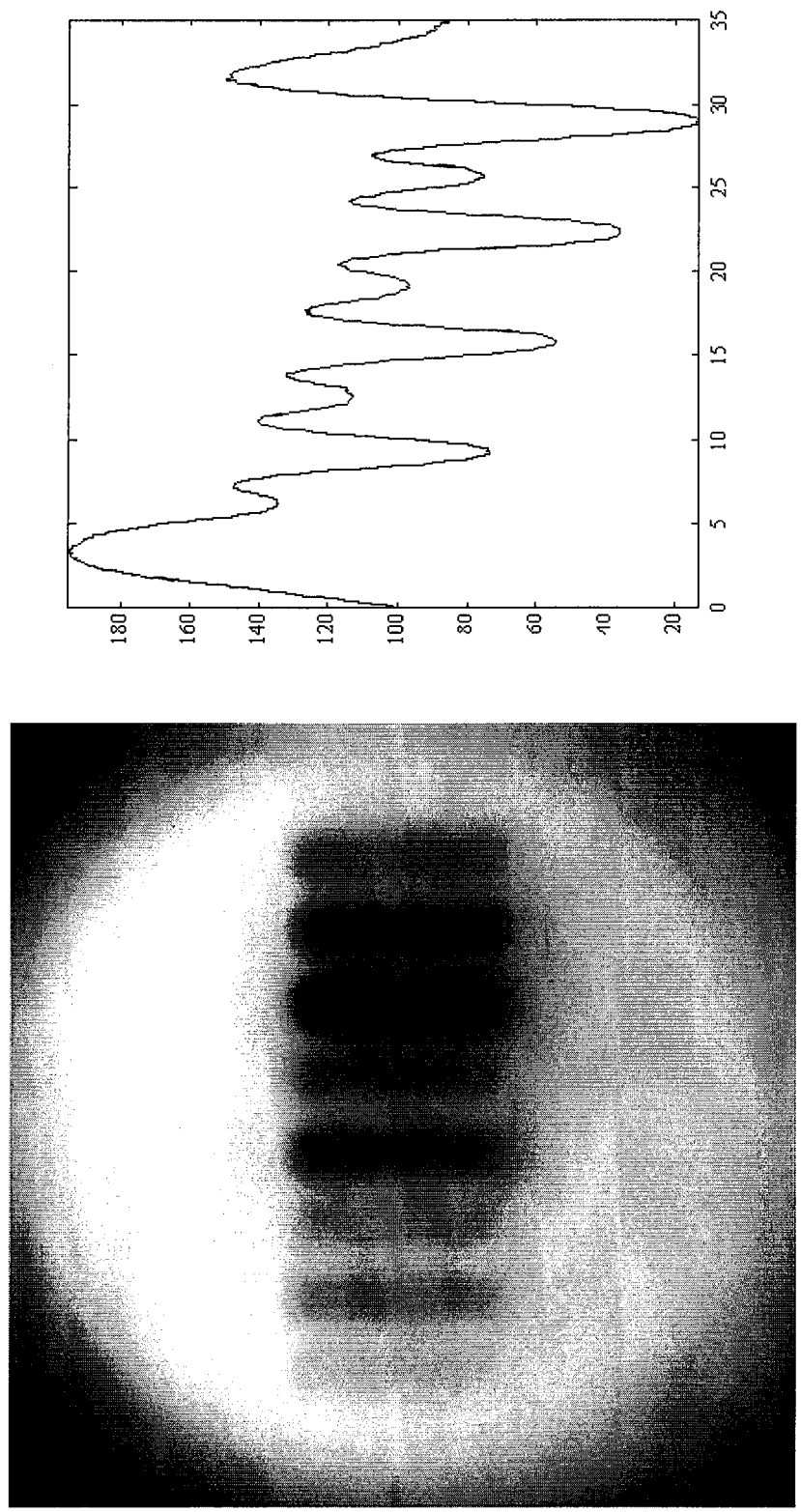

FIG. 19 shows a confocal image of a bleached barcode, using 8 different intensity levels, in the central plane of a polystyrene fluorescent microsphere (right), and a normalized intensity profile measured through the middle code (right).

Figure 20:
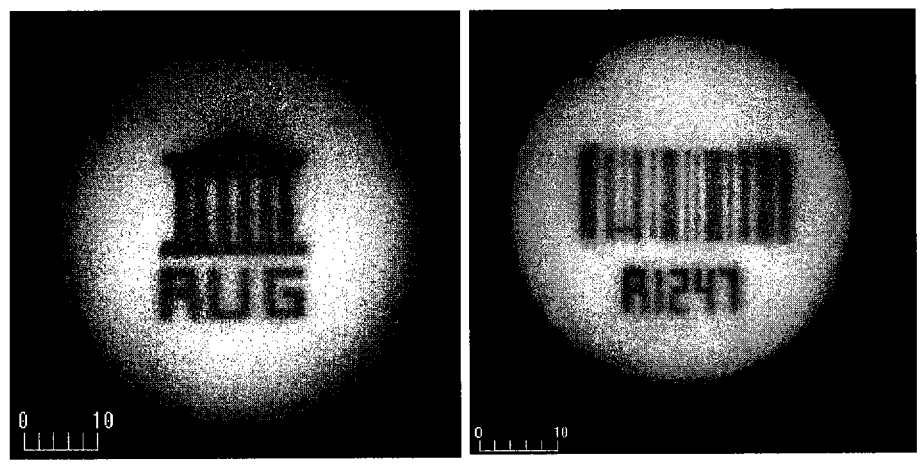

FIG. 20 shows two confocal images of microspheres wherein bar codes of different geometry e.g. letters or numbers, are bleached.

Figure 21:
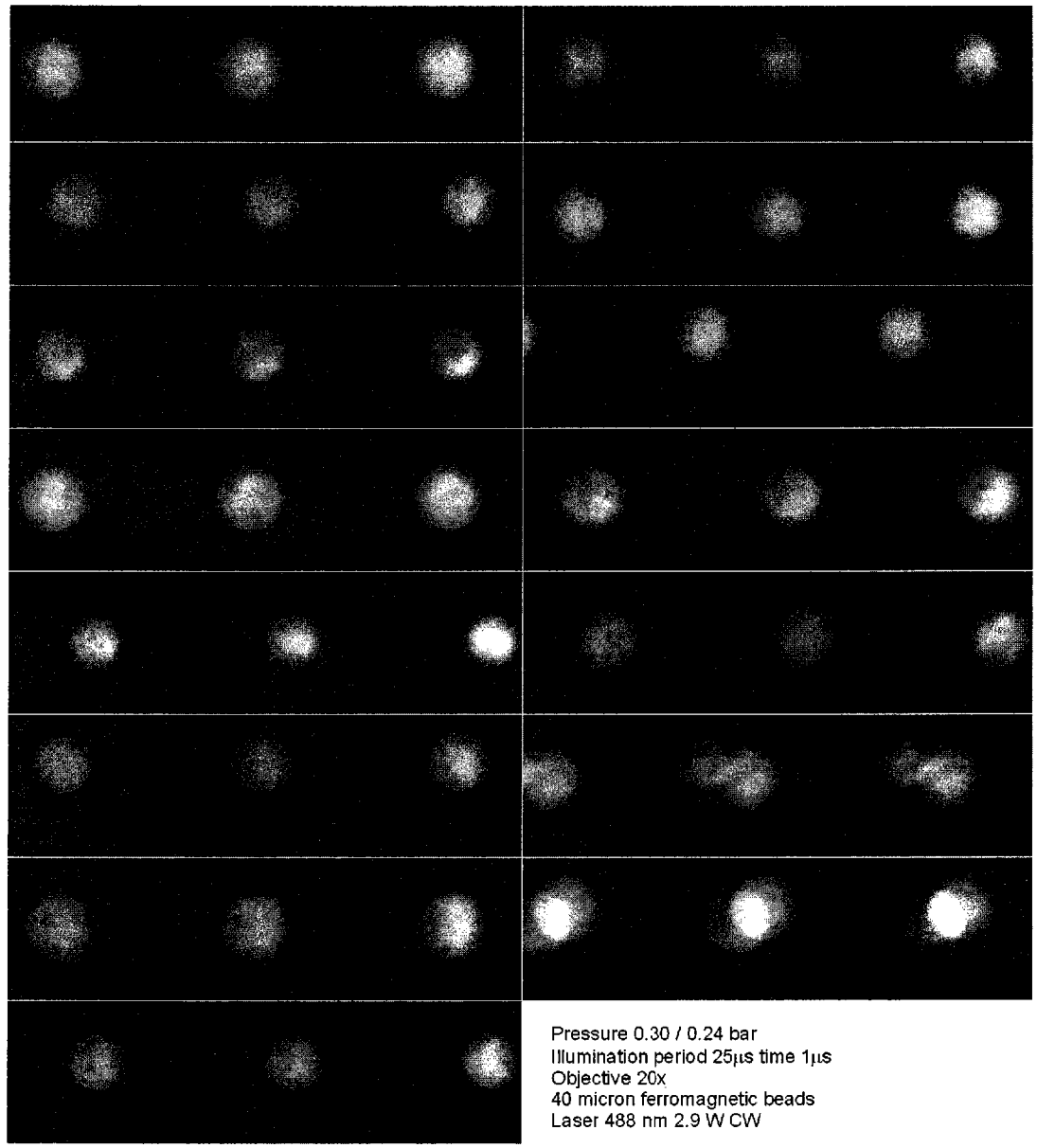

FIG. 21 shows images of 40 micron ferromagnetic fluorescent beads flowing in a flow cell.

Figure 22:
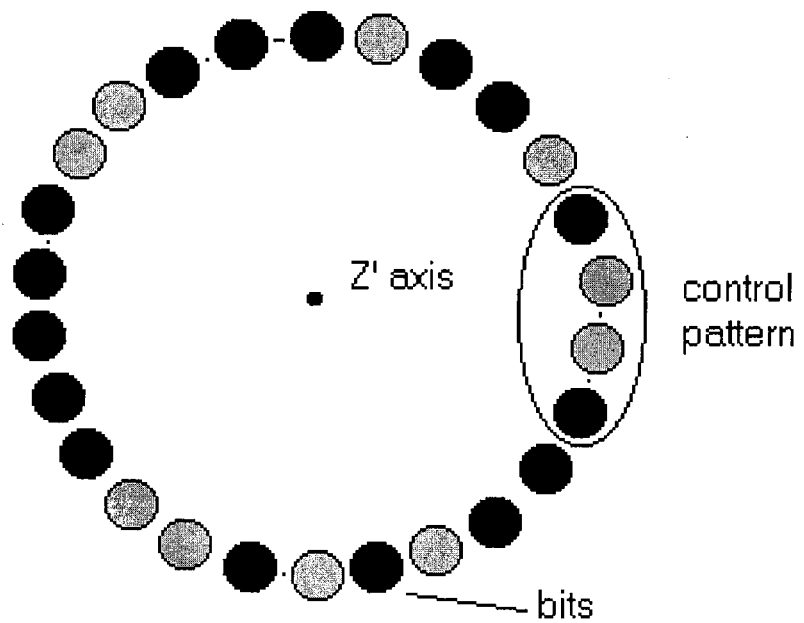

FIG. 22 represents a cylindrically symmetric bead wherein the codes are written in a circle around the Z' axis, with a control pattern which indicates the beginning of the code.

Figure 23:
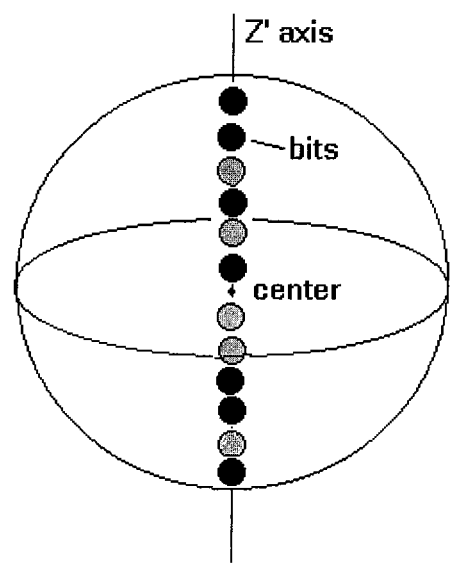

FIG. 23 represents a spherical bead wherein code bits are written along the symmetry axis of said bead.

Figures 24, 25:
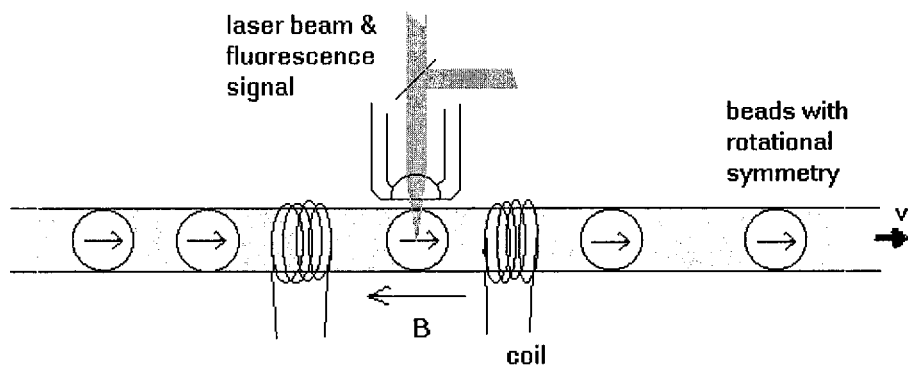

FIG. 24 shows magnetic beads flowing through a capillary, and passing through the focus of a laser beam. Coils, carrying an electric current, create a magnetic field and orient the beads along the direction of motion.

FIG. 25 shows an example of a coding scheme using 4 different intensities, each intensity represented by a color and a number from 0 to 3. This coding scheme has 28 characters, symbolically represented by the 26 letters of the Roman alphabet and two extra punctuation marks. Each character consists of 4 coding elements (i.e. 4 possible intensities (or colors)) with the extra condition that no two identical elements may follow each other, not even when two characters are placed next to each other.

Figure 26:
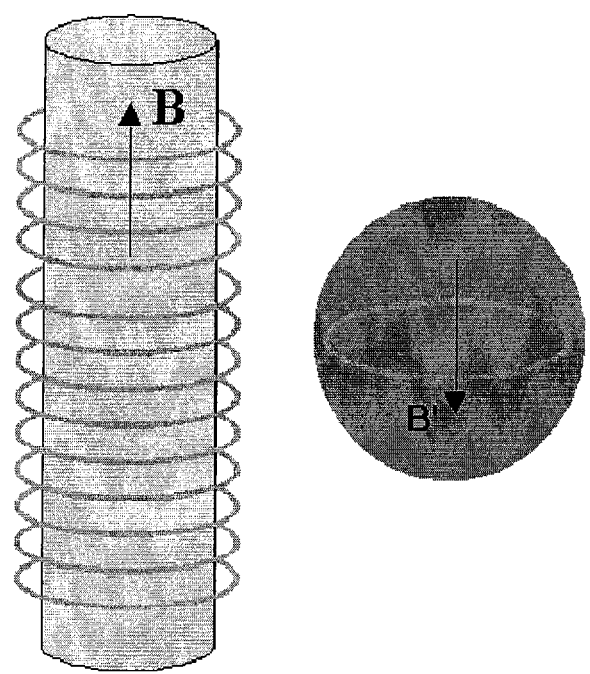

FIG. 26 represents a capillary surrounded by a coil generating a variable magnetic field B and a bead containing a closed conductor with induced magnetic field B', which is parallel when the magnetic field B is increasing.

Figure 27:
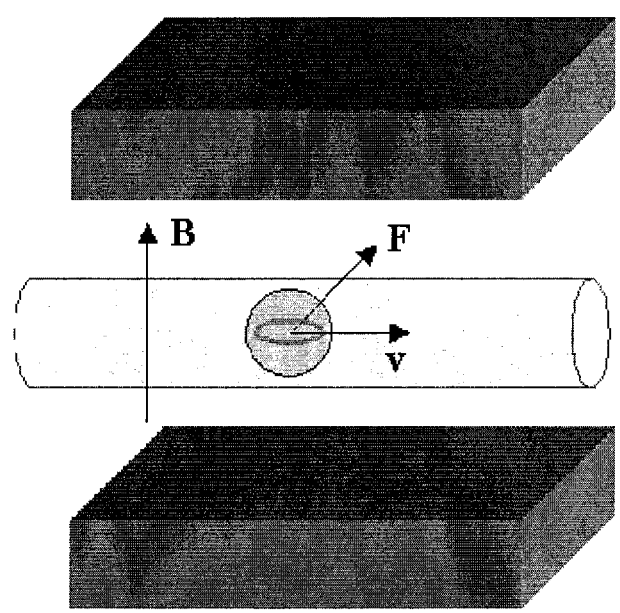

FIG. 27 represents a bead containing a closed conductor flowing in a capillary that is placed between two magnetic plates and submitted to a magnetic field perpendicular to the flow direction.

Figure 28:
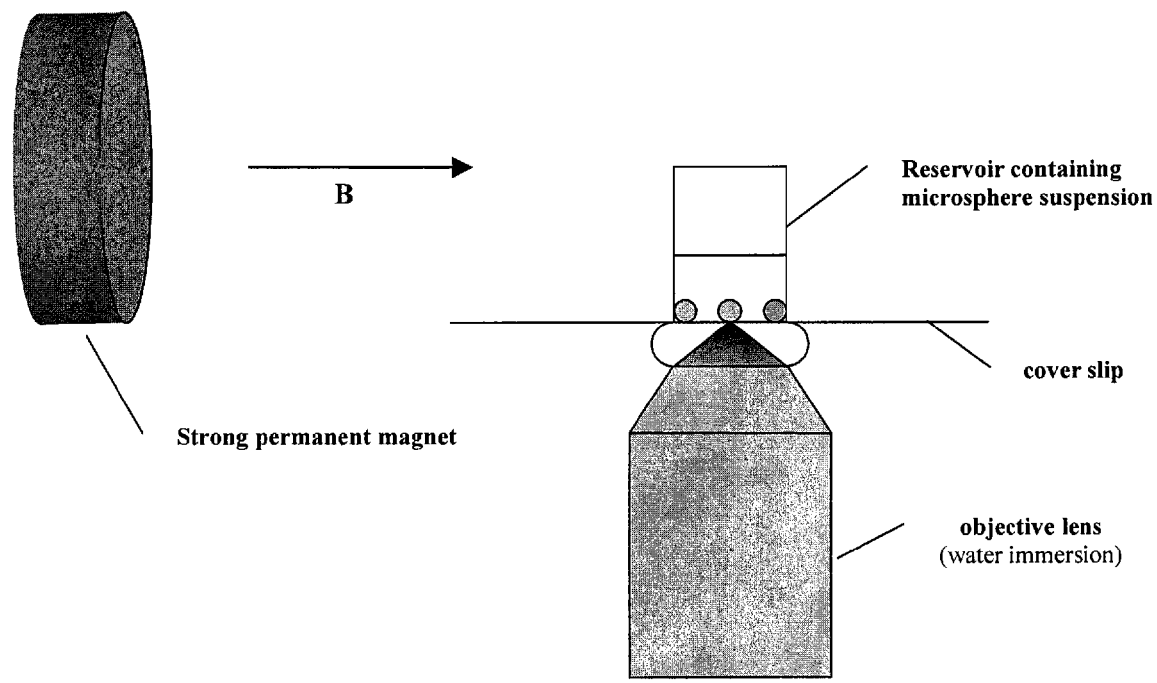

FIG. 28 represents a schematic drawing of an experimental set-up wherein a reservoir containing ferromagnetic green fluorescent microsphere suspension was placed on a Bio-Rad MRC1024 confocal microscope attached to an inverted microscope so that it was possible to use a Nikon 60× water immersion objective lens to look at the beads through the bottom microscope slide. The microspheres were illuminated by a 488 nm laser beam. The microspheres were oriented by an external magnetic field B induced by a strong permanent magnet positioned 20 cm from the reservoir.

Figure 29:
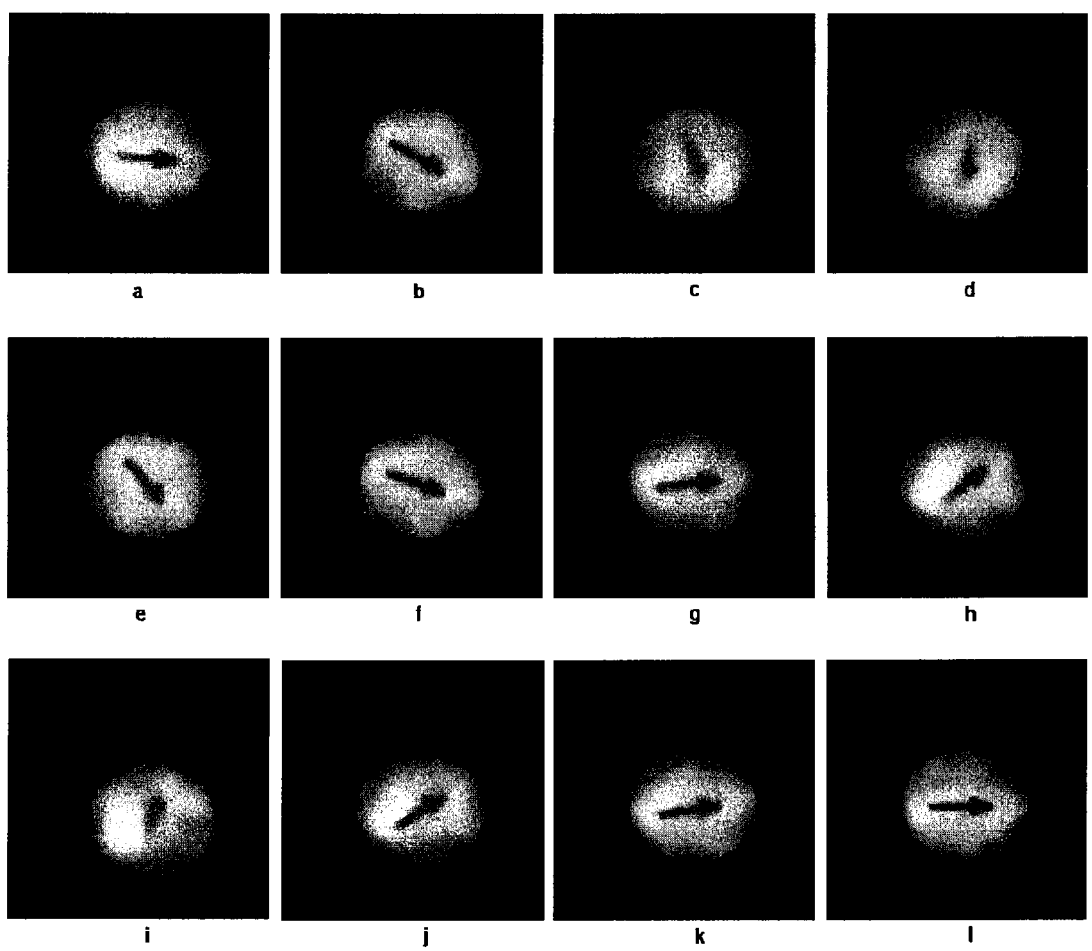

FIG. 29 represents images of ferromagnetic microspheres wherein an arrow was bleached at the central plane said microsphere. In image (a), the microsphere was oriented in an external magnetic field of a magnet. In images (b-i), the microsphere was oriented in a second moving external magnetic field. In images (j-l), the microsphere returned to the original orientation after taking away the second magnet.

Figure 30:
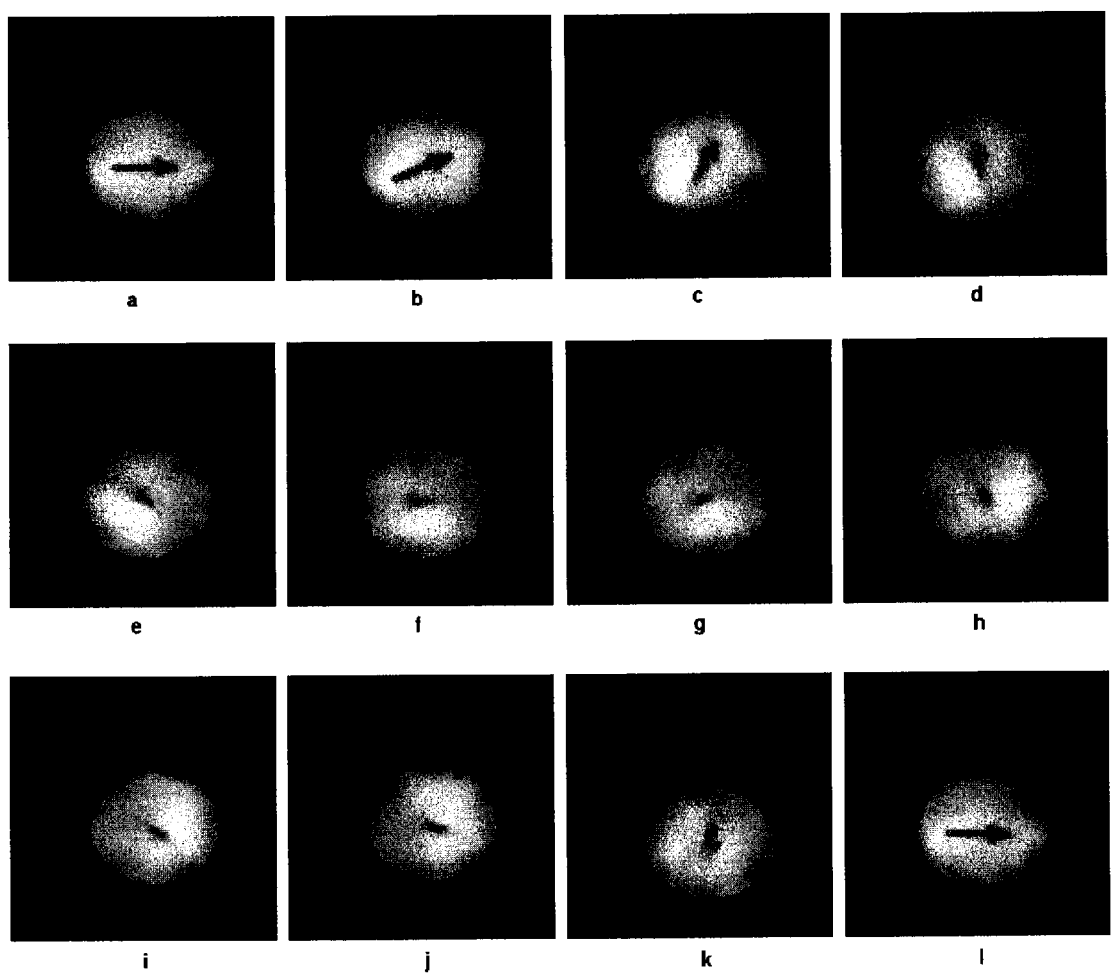

FIG. 30 represents images of ferromagnetic microsphere wherein an arrow was bleached at the central plane said microsphere. In image (a), the microsphere was oriented in an external magnetic field of a magnet. In images (b-j), the same magnet was used to rotate the microsphere by moving 360° around the reservoir and placing it back in its exact original position. Image j shows that the microsphere did not return to its original orientation due to a relatively strong polymer-glass interaction. In images (k-l, the microsphere was loosened by quickly moving a second magnet near the reservoir and was observed to return immediately to its original orientation.

Figure 31:
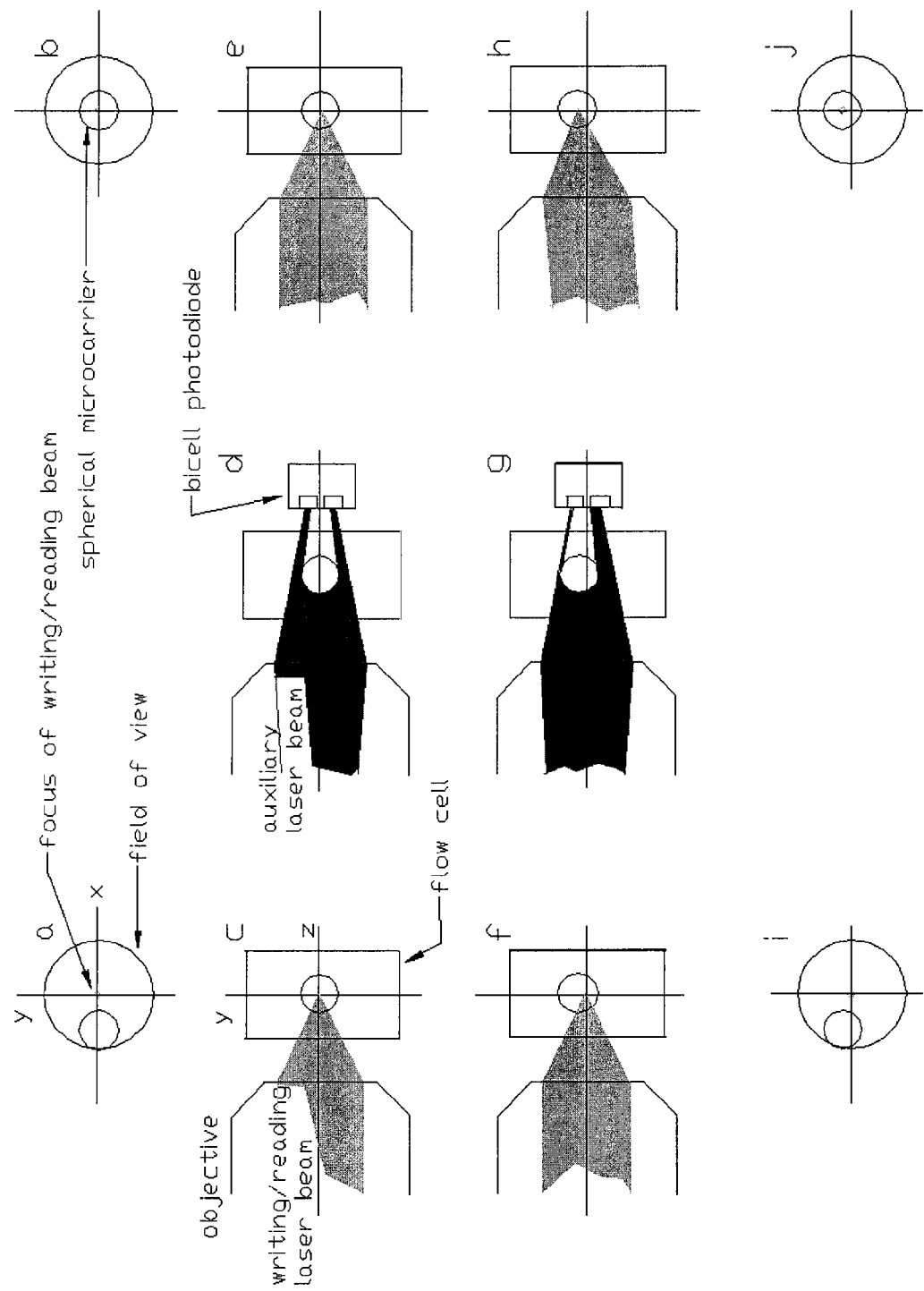

FIG. 31: Drawings (a, b, i, j) represent schematic field of views of a microcarrier flowing in front of a microscope objective. Drawings (a,i) show the field of view before the microcarrier arrives into the focused laser beam for reading/writing the code. Drawings (b,j) show the field of view with a microcarrier at the focus position. Drawings (c,d,e,f,g,h) represent side view of the microscope objective placed in front of a flow cell. Drawing (c) shows the case where the focus of the reading/writing laser beam scans along the symmetry axis of the microcarrier. Drawing (f) shows the case where the focus of the reading/writing the laser beam scans below the symmetry axis of the microcarrier. Drawing (d,g) represents the case where an auxiliary laser beam illuminates a microcarrier and produces a shadowing effect on the other side of said micro carrier.

In order that those skilled in the art will better understand the practice of the present invention, examples of the present invention are given below by way of illustration and not by way of limitation.

1. Examples of positioning and orienting a microcarrier using a solid support.

Using such preferred microcarriers as mentioned above, two preferred embodiments to position and orient a microcarrier are disclosed. Firstly, the microcarriers are collected on and transported by a solid support, and in the second preferred embodiment, the microcarriers are transported by the flow of a fluid or semi-solid medium.

Figure 1:
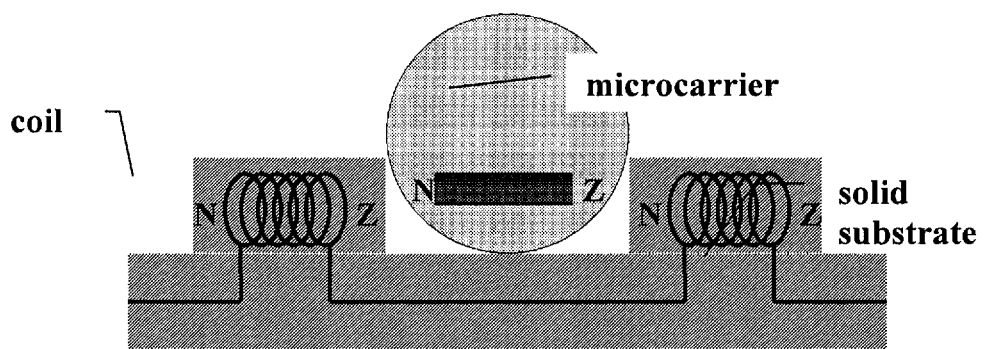

The solid support has wells with such a shape that the microcarrier fits in it in only a particular or a limited way thus obtaining a certain orientation. The wells can be magnetic in order to hold a magnetic microcarrier into place and to orient it in a certain way. One configuration is given as an example in FIG. 1. Other possibilities are the chemical and/or biological interactions between the solid support and the microcarrier.

The wells in the support can further be provided with vacuum channels in order to keep the microcarriers into place. The support can be flat and magnetic/electrically charged if only collection of magnetic/charged microcarriers is needed. The microcarrier can be a combination of the possibilities mentioned above. The wells mentioned above, can be ordered in a certain pattern on the solid support, e.g. one row, 2D array, spiral, concentric rings, etc.

The wells can also have a non-spherical configuration for example conical or ellipsoidal such that non-spherical microcarriers will be housed in the wells in a specific orientation.

2. Examples of positioning and orienting a microcarrier using means for transportation such as a flow of a fluid.

The microcarrier can be transported by a fluid flowing through a channel, e.g. a capillary. In literature (ref. 1-6) it is shown theoretically by 2D computer simulations that a spherical or ellipsoidal particle will be positioned at a certain depth when flowing through a channel. It is also theoretically shown that an ellipsoidal particle will have a precise orientation depending on the exact circumstances. It is for example possible that an ellipsoidal particle of the right ellipticity flowing in a capillary with the right diameter, will be positioned on or near the central line with its longest axis parallel to the flow. In that way, the only remaining freedom of movement, is a rotation about its longest axis.

The next paragraph explains a preferred embodiment of the method in detail, wherein this positioning and orienting of microcarriers is obtained by a fluid flow.

If an ellipsoidal particle is additionally provided with a dipole moment perpendicular to its longest axis, the rotational freedom about this axis can be eliminated as well when applying an electric or magnetic field perpendicular to the flow direction.

Figure 2:
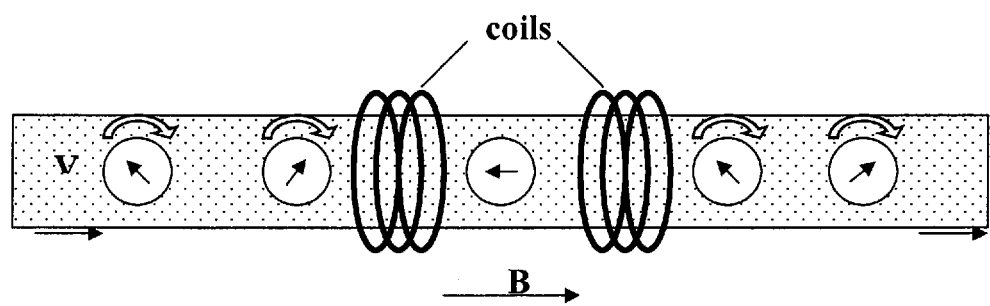

If a spherical microcarrier is transported in a fluid, it will normally rotate. This rotation can be eliminated using microcarriers with a magnetic or electric dipole moment and applying a suitable magnetic/electric field. This is illustrated in FIG. 2. Spherical microcarriers with a magnetic dipole moment are transported by a fluid through a capillary. Due to its movement relative to the flow, a rotational force will act on the carrier. When the carriers pass through the region between the two coils, the rotational force will be compensated by the magnetic force acting upon the dipole moment and trying to position the micro carrier as illustrated (dipole moment antiparallel to the magnetic field B). Thus the spherical microcarrier is positioned by the flow and oriented by the magnetic field, leaving only rotational freedom about its dipole axis.

The situations described above can additionally be provided with an asymmetric mass distribution in order to eliminate the last degree of rotational freedom making use of the gravitational or centrifugal force.

Experimental investigation of the positioning of spherical microcarriers flowing in a fluid, for example water through a capillary tube.

Using a confocal microscope as detection means, the inventors have examined the movement of particles in a laminar flow inside a capillary.

Spherical fluorescently labeled polystyrene microparticles (in this first experimental part not magnetic) of 15 µm diameter suspended in distilled water were used and imaged by a confocal microscope such fluorescent particles can be easily viewed.

Figure 3:
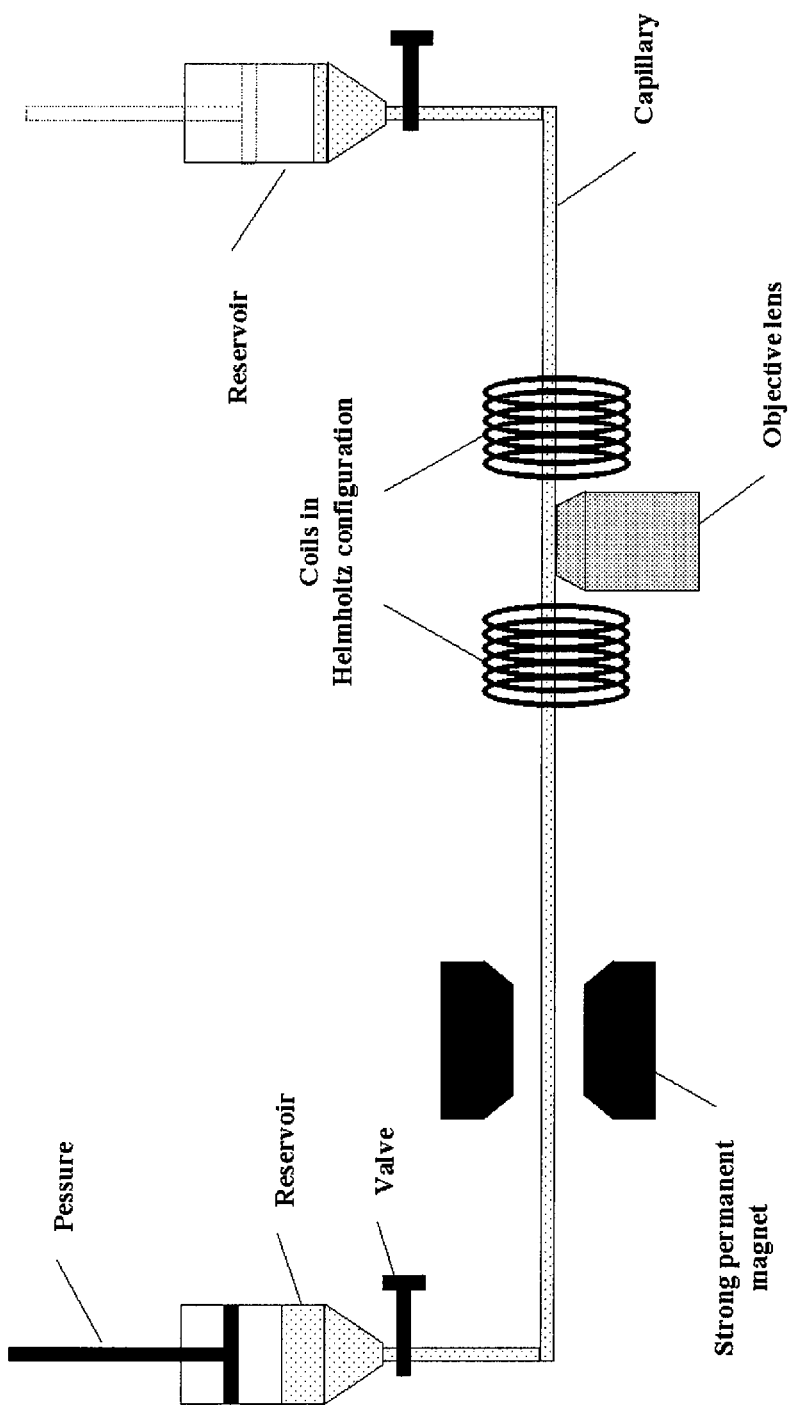
Figure 4:
Figure 5:
Figure 6:
Figure 7:

A capillary system was made that fitted onto the confocal microscope. The capillary itself is made of glass and has a square shape. The internal dimensions are 80 µm×80 µm and the outer dimensions are 180 µm×180 µm. In FIG. 3 this setup is schematically shown. The capillary is at both ends connected to a reservoir. The suspended microparticles can be brought in this reservoir. A constant pressure can be applied to the reservoir thus causing the suspension to flow to the other side. A low pressure (<0.2 atm) is preferably used in order to create a laminar flow in the capillary.

The particles are imaged when passing the objective lens of a scanning laser confocal microscope. In this first experiment no electric or magnetic fields were applied. The objective lens used has a numerical aperture of 0.45 and a ten fold magnification. This lens was used in order to have a large field of view.

When the particles are flowing, images are taken during a certain time interval, typically about 1 minute, thus obtaining a time series. Afterwards these images are added together into one picture showing all the particles that have passed during that time interval. That way it is possible to see whether or not the microcarriers are flowing along the same path.

These experiments show that the particles are indeed positioned along a constant path when being transported by a laminar flow inside a capillary, as predicted by 2D computer simulations. More testing at a higher resolution is of course necessary to examine the magnitude of possible fluctuations. More experiments are needed to see the effect of changing the particle size.

In a further experiment microcarriers having a magnetic dipole moment were used in the previously described setup and a magnetic field B was imposed on the transported micro carriers via the two coils in the Helmholtz configuration (FIG. 3). The magnetic field extends parallel to the capillary tube. A rotation restriction was observed as explained in FIG. 2.

These experiments prove that the method of the invention can provide a specific defined position of a microcarrier useful for identification purposes.

3. Examples of magnetic microcarriers.

Green fluorescent 40 µm microspheres coated with a ferromagnetic coating ($CrO_2$) were used. Ferromagnetic microspheres or microcarriers are the primary candidates to obtain a correct orientation in the fluid flow by using an external magnetic field parallel to the flow, as previously explained. This experiment determines if said microcarriers are still transparent enough to "see" the central plane and to write patterns inside by for example photobleaching.

In this experiment, the ferromagnetic microspheres were suspended in de-ionized water, deposited on a microscope slide, and covered with a cover slip. The particles were then imaged using a Bio-Rad MRC1024 UV confocal microscope. The objective lens used was a Nikon Plan Apochromat 60× N.A. 1.4 water immersion lens. The light source for excitation of the green fluorescent microspheres was a Spectra Physics Stabilite 2017 Ar-ion laser tuned to the 488 nm line.

Figure 8:
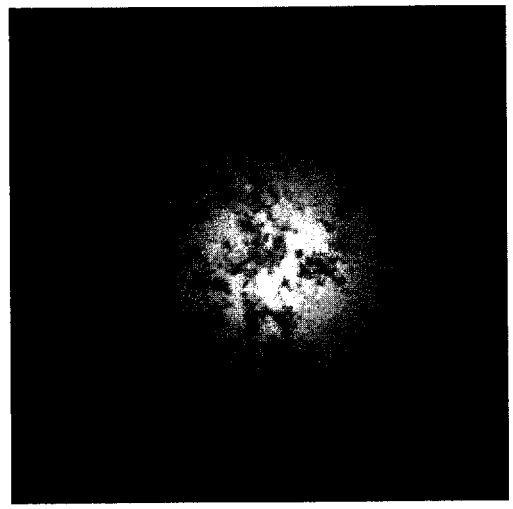
FIG. 8 shows a confocal image of the top of a green-fluorescent 40 μm microsphere coated with ferromagnetic CrO2 particles.

FIG. 8 shows a confocal image focused on the top of a ferromagnetic coated microsphere. It can be seen that the coating consists of a layer of submicron $CrO_2$ particles deposited on the surface of the microspheres. Since the $CrO_2$ particles are non-fluorescent and non-transparent, they show up as dark specks against the bright fluorescent microsphere.

Figure 9:
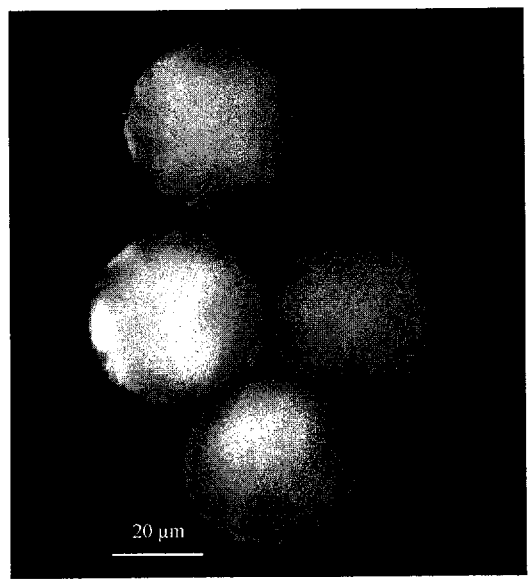
FIG. 9 shows a confocal image of the central plane of 40 μm green fluorescent ferromagnetic-coated particles.

To evaluate the transparency of the microspheres coated with the ferromagnetic particles, a confocal image of the central plane of some microspheres was taken (FIG. 9). The central plane was imaged very clearly, indicating that the coated microspheres were still transparent. Compared to uncoated microspheres, the recorded fluorescent signal was less homogeneous across the central plane.

Figure 10:
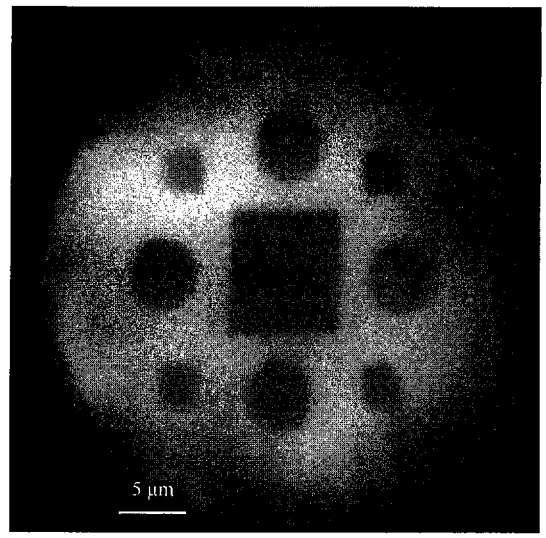
FIG. 10 shows a confocal image of a simple pattern that was bleached at the central plane of a ferromagnetic-coated particle.

Next, the encoding by photobleaching of the ferromagnetic-coated microspheres was evaluated. The microscope was focused on the central plane of a coated microsphere and a bleaching pattern with basic geometric forms was drawn using dedicated software especially designed for bleaching experiments. The light power in the sample was about 20 mW. The geometry of the bleaching pattern was of no importance in this experiment since the sole purpose of the experiment was to check if the coated particles could still be bleached or not. FIG. 10 shows that the pattern could easily be written inside the coated microsphere.

In conclusion, green fluorescent 40 µm polystyrene microspheres were coated with ferromagnetic $CrO_2$ particles. Despite the non-transparency of those ferromagnetic particles, the coated microspheres still proved to be transparent. The recorded fluorescence was less homogeneous when compared to uncoated particles because the ferromagnetic particles at the surface of the microspheres blocked part of the light pathway. However, the concentration of ferromagnetic particles could be altered thus improving the homogeneity of the recorded fluorescence. The minimal concentration could be determined by the magnetic force needed to orient the microcarriers flowing through the positioning device. The ferromagnetic microspheres were easily encoded by bleaching a pattern at the central plane.

4. Examples of photochromic microcarriers

An alternative to encoding by photobleaching is encoding by photochroming. Polystyrene microspheres were loaded with the photochromic compound 1,2-Bis(2-mehoxy-5-pbenyl-3-thienyl)perfluorocyclopentene (Extraordinary Low Cycloreversion Quantum Yields of Photochromic Diarylethenes with Methoxy Substituents, Shibata K, Kobatake S, Irie M, Chem. Lett. (2001), vol. 7, 618-619) which has initially no absorption in the visible range, but develop an absorption band extending from about 450 nm to 750 nm after UV illumination, with an absorption maximum near 600 nm.

Consequently, the loaded microspheres were initially transparent, and turned blue upon UV illumination.

Encoding a microsphere by photochroming is considered as an alternative to encoding by photobleaching mainly because it makes it easier to read the code, requiting less stringent demands about the precision of the positioning device. In fact, when a bleached code is used, we have a completely fluorescent microcarrier in which only a small region has no signal. Consequently, the identification of said encoded microsphere requires the use of a confocal microscope and also requires bringing the plane where the code was bleached exactly into focus. When encoding by photochroming, we obtain a completely transparent microcarrier in which a colored pattern is written. This is much easier to detect and there is therefore no need for a confocal microscope, a standard light microscope is sufficient. Moreover, using the same laser power, the process of photochroming is faster than photobleaching.

In this example, polystyrene microspheres were loaded with the photochromic compound. Next, a first attempt is made to write a pattern inside the photochromic microspheres.

All the experiments were performed under dark room conditions. Unloaded transparent 28 µm polystyrene microspheres (5% crosslinking degree) where loaded with the photochromic compound 1,2-Bis(2-methoxy-5-phenyl-3-thienyl)-perfluorocyclopentene. First, 5 mg of dry microspheres were suspended in a 2% (w/v) solution of the photochromic compound in $CH_2Cl_2$ and were incubated overnight. The suspension was then centrifuged during 5 minutes at 12000 rpm. After the centrifugation, the floating spheres were isolated by removing the underlying liquid. The spheres were then suspended in de-ionized water and applied on a microscopic slide for observation under the microscope.

The microscope was setup as described in example 3. A Coherent Enterprise laser was further used to color the microspheres (357 nm UV line) and the 647 nm line of a Bio-Rad Ar/Kr laser was used for imaging the microspheres. Red light was used because it is absorbed by the blue regions resulting in a gray scale image where the blue regions are dark and the transparent regions bright. The images were recorded in transmission light mode by using a transmission light detector.

Figure 11:
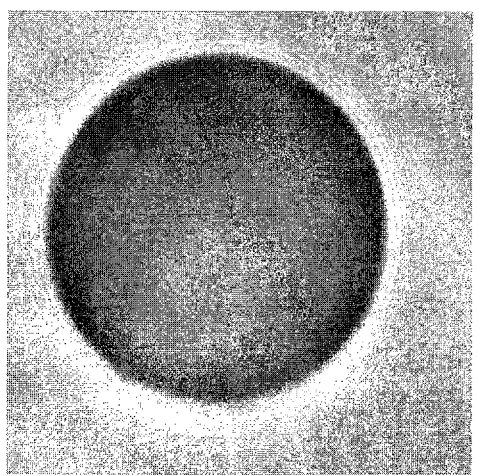
FIG. 11 shows an image of a 28 μm photochromic microsphere (before UV illumination) with red light in transmission light mode. The microscope was focused at the central plane.

To design an encoding pattern, a partial region of the microsphere was scanned with an UV light by zooming into that region and performing a regular image scan. This resulted in a written square (vide infra). FIG. 11 shows a 28 μm photochromic microsphere imaged in transmission light mode using a red laser line (647 nm). At this stage, the microsphere was not exposed to UV light. The darkening along the edges was due to lens effects of the spherical microsphere (refraction index 1.59) suspended in water (refraction index 1.33).

Figure 12:
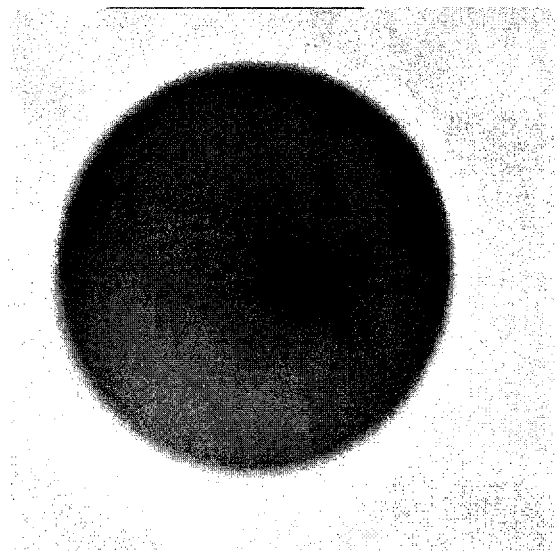
FIG. 12 shows a transmission image of the microsphere after photochroming of a 3 μm square in said microsphere.
Figure 13:
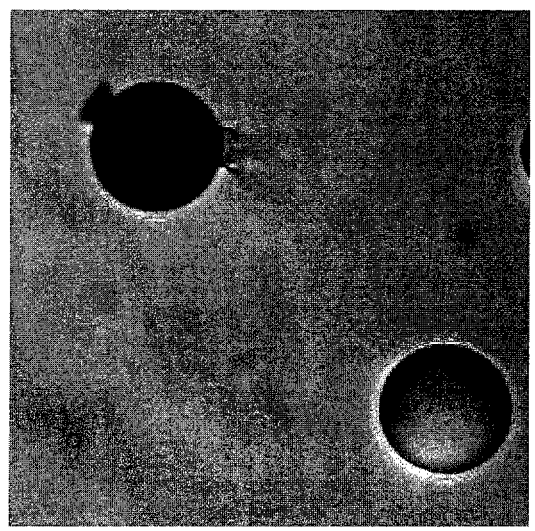
FIG. 13 shows a transmission image of a completely colored and transparent microsphere.

After zooming into a small region (3×3 gra) of the central plane of the microsphere, a scan was performed using the 357 nm UV line at 0.5 mW. An image was then taken with the red laser line (FIG. 12). A dark square was clearly visible indicating that the microspheres were successfully loaded with the photochromic dye that turned blue upon UV illumination. The blue square only transmits 50% of the red light compared to the transparent surroundings. As illustrated FIG. 12, upon UV illumination, the microsphere became darker then before UV illumination (FIG. 11). For comparison purposes, FIG. 13 shows two microspheres, one completely colored (dark sphere) after UV illumination and a second one that was not exposed to UV light.

In conclusion, the microspheres were successfully loaded with the photochromic compound. Less laser power (~40×) was needed to color said microspheres, when compared to photobleaching. The advantage of this encoding method is that the codes can be written faster.

5. Examples of fluorescent microcarriers

According to an embodiment of the positioning and orienting device, the microcarriers are transported by a fluid flow and pass the writing beam only once and in one direction only. Therefore, the preferred code is a one-dimensional "dotcode" rather than a barcode (which is a one-dimensional code as well, but written in two dimensions). This experiment determines if it to write such a "dotcode" by photobleaching at the central plane of a 40 μm microsphere, and check whether the bleaching process is fast enough for a code to be written by scanning only once.

In this experiment, 28 μm polystyrene microspheres (5% cross-linking degree) loaded with the fast bleaching green fluorescent dye NODD (N-(7-Nitrobenz-2-oxa-1,3-diazol-4-yl)diethyl amine) were used.

To simulate the flowing of a microsphere past a writing beam, the microsphere was positioned under a confocal microscope that was focused on the central plane of said microsphere. Next, the instrument was set to scan only one line across the sphere thus simulating a positioned microsphere passing a stationary writing beam. Using dedicated software, the instrument was programmed to switch the laser power on and off a couple of times during the linescan in order to obtain a "dotcode".

Figure 14:
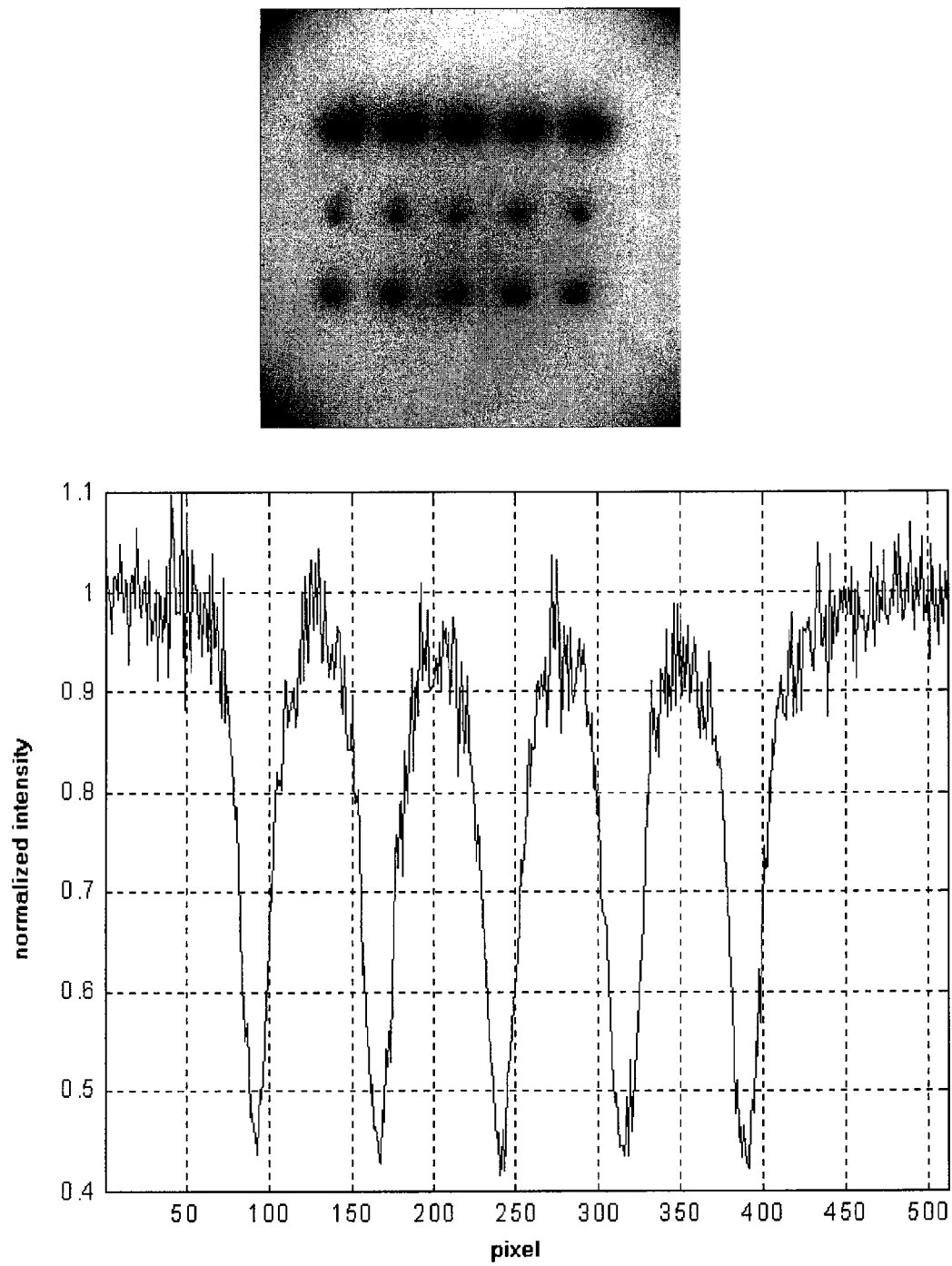
FIG. 14 shows a confocal image of three 'dotcodes' microsphere (left) and a normalized intensity profile measured through the middle code (right). Each division along the image axes is 2 μm.

The scanned line consists of 512 pixels and in this experiment 1 pixel corresponds to 0.038 μm. One linescan takes 1.2 ms which means a scanspeed of 16.35 μm/ms. This experiment simulates the situation where a microsphere is flowing past a stationary writing beam at a speed of 16.35 μm/ms, or a maximum of 584 spheres (28 μm) per second. Using a dedicated software the instrument was programmed to switch the laser 5 times to 20 mW (in sample) during 8 pixels (i.e. 0.304 μm) and 80 pixels between each flash. A code was obtained consisting of five dots of 3.04 μm apart. The result is shown in FIG. 14, as a dotted line in the middle of a microsphere. Under the conditions used, about 55% bleaching was obtained. The top and bottom line were obtained by bleaching respectively 40 and 16 pixels resulting in a bleaching level of 80% and 70%.

In conclusion, 20 mW laser power in sample was sufficient to create a 'dotcode' at the central plane of a NODD loaded microsphere with a bleaching level of over 50%. The scanspeed was 16.35 μm/ms. This experiment demonstrates the feasibility of the encoding of a dotcode by photobleaching by using one linescan. It is also possible to increase the scanspeed and obtain the same amount of bleaching, by increasing the laser power in sample.

The next step in the experiment, consisted in checking the stability of the bleached code inside a fluorescent microcarrier under solvent conditions, more specifically when the microcarriers are suspended in a DMSO (dimethylsulfoxide) solution.

The NODD loaded 28 μm microspheres of the previous experiment were used. First they were suspended in de-ionized water, then a drop of this suspension was applied to a microscope cover slip and air dried, leaving the spheres attached to the coverslip. The microspheres were then covered with a drop of DMSO (>99.7%) and placed under a confocal microscope.

Figure 15:
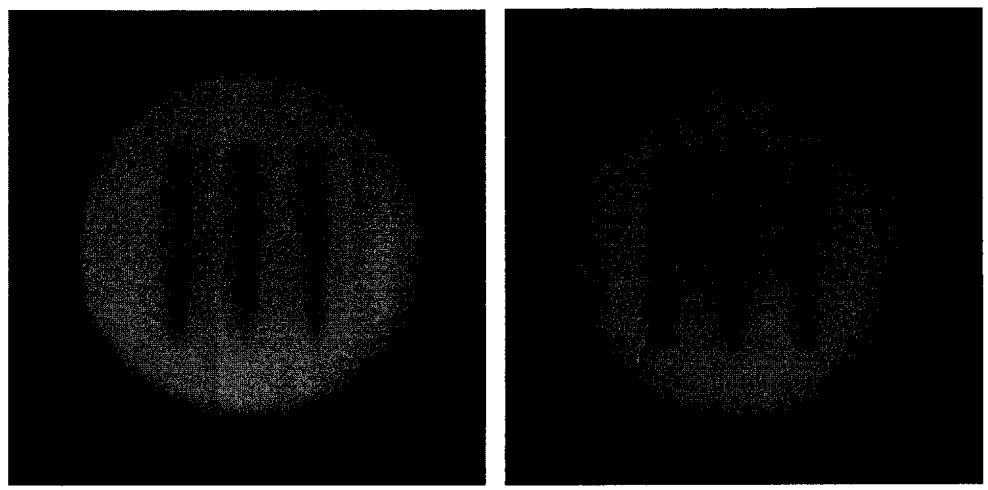
FIG. 15 shows a confocal image of a photobleached microsphere in DMSO (left). The second image on the right was taken three hours later.

A simple pattern was bleached at the central plane of a microsphere and was imaged again after three hours to check for any difference in the fluorescence of the microsphere or the bleached pattern. The confocal microscope was focused at the central plane of a microsphere surrounded by DMSO. A simple pattern, consisting of three lines, was bleached. After three hours, the pattern was imaged again. The results are illustrated FIG. 15. No difference could be found in either fluorescence or bleached pattern. The left image was less sharp because of a slight misfocus on the pattern.

No difference could be found in either fluorescence of the microsphere or bleached pattern after being suspended in 99.7% DMSO for three hours. This demonstrates the high stability of the written pattern, which is independent of the assay conditions.

6. Examples of positioning and orienting a microcarrier in a liquid or semi-liquid support.

FIG. 16 represent microcarriers positioned in a semi-liquid or a liquid support, wherein said semi-liquid or liquid support is composed of two semi-liquids or liquid media with different density. The micro carrier are positioned at the interface of the two media. Two coils are provided that can induce a magnetic field. Inside the coils, the magnetic field will try to align the dipole moment antiparallel to itself, thus orienting the microcarrier in a specific manner, allowing thereby the easy detection of the codes. The absence of a flow in said distribution of the microcarrier results in the possibility that the detection means could be mobile.

7. Examples of different types of codes.

Performing bead based assays on very large numbers of compounds or molecules in drug discovery and drug screening, requires labeling of each of the microcarriers according to the particular ligand bound to its surface. This allows the further mixing of the uniquely encoded microcarriers and subjecting them to an assay simultaneously. Those microcarriers that show a favorable reaction of interest between the attached ligand and target analyte may then have their code read, thereby leading to the identity of the ligand that produced the favorable reaction. Two different ways of encoding microcarriers are presented here, providing a virtually unlimited amount of unique codes.

Photobleaching: According to the first method, a pattern is written in a homogeneously fluorescently dyed microcarrier by means of photobleaching. This is a photo-induced process through which the fluorescent molecules lose their fluorescent properties resulting in a fading of the color. This can be done by first focussing a Confocal Laser Scanning Microscope (CLSM) at a certain depth into the microcarrier where the pattern, designed in dedicated software, is going to be written. The CLSM is modified by adding a powerful laser combined with a fast optical switch, which controls the power of the laser light reaching the microcarrier. Low power is used for mere imaging, while high power is used for fast bleaching. The apparatus set up is schematically represented FIG. 17.

While subsequently taking an image, which is done by scanning the laser light in a raster pattern, dedicated software controls the optical switch in such a way that low and high power laser light reaches the microsphere according to the designed pattern. Since the fluorescent molecules are virtually immobile in the microcarrier matrix, the bleached regions will stay, resulting in a bright background and a darker permanently bleached pattern. FIG. 18 shows a confocal image of a bleached barcode, using three widths and two intensity levels, in the central plane of a 45 micron polystyrene fluorescent microsphere. FIG. 19 shows a confocal image of a bleached barcode, using 8 different intensity levels, in the central plane of a polystyrene fluorescent microsphere (right), and a normalized intensity profile measured through the middle code (right).

The second method uses the same technique, except that the process of photochroming is used instead of photobleaching. Here the microcarriers are homogeneously dyed with a photochromic compound which changes color upon radiation of light with the appropriate wavelength. For example, the microcarriers can be initially colorless and transparent, but will carry a colored pattern inside at a certain depth after radiation using essentially the same instrument as described above.

The amount of codes depends on a number of factors: the resolution of the writing beam, the amount of intensity levels used, the available space in the microcarrier, the dimensions of the code design, etc. For example, using a 60× NA1.4 objective lens, we have proved that it was possible to create at least 263·106 different codes over a length of only 16 micron with just a one dimensional code using two different widths and 4 intensity levels (results not shown). This code could easily be written in the central plane of a 30 micron microsphere. Many more codes can be generated if e.g. larger microspheres are used or if the code design is extended to two or three space dimensions. Examples are shown FIG. 20 wherein bar codes of different geometry e.g. letters or numbers, were bleached on two microspheres. Therefore, it is fair to state that the amount of codes that can be generated using this technique is virtually unlimited.

8. Experimental investigation of the positioning and orientation of ferromagnetic fluorescent beads flowing in a fluid in a flow cell.

In this example, 40 micron ferromagnetic fluorescent beads were flowing in a flow cell. The flow speed was around 6 m/sec. The pressure was between 0.30 and 0.24 bar. Images of said beads are shown FIG. 21. The light source for excitation of the fluorescent beads was a laser tuned to the 488 nm line. The objective lens used had a twenty-fold magnification. The flowing beads were imaged using a camera having a shutter time of 50 milliseconds, and a one microsecond light-pulse illuminated the flow every 25 microseconds. Because of this setting, each flowing bead can be seen two or three times in each image. In FIG. 21, on the bottom-right, is an image of a bead passing twice while the shutter was open. The image above the aforementioned image represents a cluster of two beads.

9. Encoding beads by photobleaching and further positioning and orienting of said beads.

Fluorescent beads can be encoded by means of photobleaching under a microscope. Information can be written in 3 dimensions by scanning the focus of the writing/reading beam along the X,Y,Z axis with the Z axis being parallel to the optical axis of the microscope. a maximum of 60 bits of information may be found along 1 axis, assuming that in practice there is 32 bits, this provides with the possibility to write $4 \times 10^9$ different codes.

A mechanism is then provided to orient and position bead in its original write position. When the beads are spherically symmetric, the codes may be written as concentric spheres of equal levels of bleaching. The same information is obtained when a line is read through the center of the bead.

When a bead is a cylindrically symmetric bead (rotation symmetry along the Z') the codes can be written in a circle around the Z' axis. This allows the reading and writing essentially to 1D (($\phi$-angle in polar coordinates). A control pattern can be added, which indicates the beginning of the code as shown in FIG. 22.

Code bits can be written along the symmetry axis of a spherical bead as shown in FIG. 23. This axis is uniquely defined, once the bead is oriented. Thus, the reading can be done only along this line. The Z' axis of the bead can be either parallel or perpendicular to the optical axis of the microscope. In the case that there is no mirror plane symmetry perpendicular to the Z' axis (magnetic beads, mass anisotropy . . . ), the line can only be read in one direction. It is also possible to mark both the start and the end of the code bits.

When the reading is performed in a one-dimensional plane, it is possible to read 1000 beads per second when the following parameters are met: assuming that there are 50 bits per bead, and that 5 positions are measured per bit, this give 250 measurements per code. Since a line of 514 points can be measured in 1.2 ms (based on the specifications of the Bio-Rad MRC1024 confocal microscope), this gives 0.6 ms for reading the code of one bead, hence 1667 beads can be red per second, if the reading process is the time limiting factor.

Supplying the beads and scanning them through the focus of a laser beam can be done with the same steady motion. The steady motion can be realized in different ways. The beads can be carried along with a fluid flowing through a capillary tube. Alternatively, a capillary tube, containing the beads and (index matching) fluid, can be moved by a translation stage through the focus.

FIG. 24 shows magnetic beads, which are carried along with a fluid flow through a capillary, and are moved through the focus of a laser beam in a direction perpendicular to the optical axis of the microscope. Coils, carrying an electric current, create a magnetic field and orient the beads along the direction of motion. While moving, the codes on the beads can be written or red. Coils may also serve as indicators for arriving beads and as a velocity meter, since the moving magnetic field of the beads induces a current in the coils. The signal from the coils may thus be used to trigger the reading/writing of a bead, and as a feedback signal for controlling the bead flow.

If the flow tube is mounted vertically, the beads can also be oriented with their symmetry axis parallel to their motion, when their center of gravity does not corresponds with their geometric center. The motion of the beads can also be monitored optically. A control pattern can be added at the beginning and at the end of each code, in order to reduce the requirements on the steady flow and the precise knowledge of the velocity. The number of read/write positions can also be reduced, by using different levels of photobleaching, e.g. 0% bleached, 33% bleached, 66% bleached, 100% bleached. With this system, the flow speed can be increased and the constraints on focussing and precise positioning and orienting can be reduced. A non-limiting example of a coding scheme, using 4 different intensities, is shown in FIG. 25. Each intensity is represented by a color and a number from 0 to 3. This coding scheme has 28 characters, symbolically represented by the 26 letters of the Roman alphabet and two extra punctuation marks. Each character consists of 4 coding elements (i.e. 4 possible intensities (or colors)) with the extra condition that no two identical elements may follow each other, not even when two characters are placed next to each other.

10. Example f positioning and orientation of beads flowing in a capillary submitted to a variable magnetic field parallel to the flow direction.

The beads in this experiment contain a small closed conductor. The capillary through which the beads may flow is placed in a coil as illustrated FIG. 26. Upon passing the appropriate amount of electric current through the coil a homogeneous magnetic field B is generated. Upon variation of the electric current, the magnetic field B becomes variable.

As the bead flows through the increasing magnetic field, a current will be generated in the small conductor which in turn will generate a magnetic field B' in the bead which will act against the changes of the external magnetic field. Because a magnetic field B' is generated, a force couple will act upon the bead which aims at orienting B' antiparallel to B. An axial positioning and orientation of the bead is thus obtained, according to the direction of the magnetic field B and this without having the disadvantageous effect from the beads sticking together as a result of the permanent magnetic field. The movement of the bead is not necessary for this orientation method.

11. Example of positioning and orientation of beads flowing in a capillary submitted to a magnetic field perpendicular to the flow direction.

The beads in this experiment contain a small conductor. The capillary in this case is positioned between two polar plates, which generate a homogenous magnetic field B, as illustrated in FIG. 27. The beads are moving through the capillary with a velocity v within the magnetic B as shown FIG. 27. A Lorentz force F will act upon the electrons of the small conductor in the beads by which they will move towards one side of the conductor. The force will continue to exist as long as the beads continue to flow and as such the plane of the small conductor will be pulled in parallel with F. An axial positioning and orientation of the beads is obtained according to the direction of F. This example presents an simplified view of the forces at work in this experimental set-up.

12. Examples on the orientation and positioning of ferromagnetic microspheres

These experiments showed that the ferromagnetic 40 μm microspheres could be magnetized and oriented in an external magnetic field. In these experiments a pattern has been bleached at the central plane of a magnetized ferromagnetic microsphere while said microsphere was being exposed to and oriented by an external magnetic field. Then the pattern has been imaged while the sphere was exposed to a moving external magnetic field. It was tested whether the original orientation—known from the bleached pattern—could be found again after random movement of the microsphere when said microsphere was subjected again to the original magnetic field.

Green Fluorescent ferromagnetic polystyrene microspheres of 40 μm diameter were prepared. A 0.01% v/v solution of NP40 (a neutral detergent) in de-ionized water was made and used to make a 0.1% suspension of the microspheres. The neutral detergent was added to minimize the interaction of the polymer bead with the glass microscope cover glass (vide infra).

A reservoir was made by gluing a plastic cylinder of 0.5 cm diameter onto a microscope cover glass. The reservoir was filled with 80 μl of the microsphere suspension and the microspheres were allowed to sediment on the cover glass. The reservoir was then placed above a strong permanent magnet for 1 minute to allow the microspheres to be magnetized. Next the reservoir was placed on a Bio-Rad MRC1024 confocal microscope which was attached to an inverted microscope so that it was possible to use a Nikon 60× water immersion lens to look at the beads through the bottom cover glass. A strong permanent magnet was placed at a 20 cm distance from the reservoir in order to orient the beads without changing their magnetic polarization (FIG. 28).

An arrow was bleached at the central plane of a ferromagnetic microsphere oriented by the external magnetic field from the first strong magnet, thus indicating its original orientation (FIG. 29a). Next, the confocal microscope was set to take a series of 50 images with a 1,2 second interval between each image. While taking this series of images, a second magnet was used to move around the reservoir: first 90° to one side, then 180° in the opposite direction (FIG. 29b-i) with the first magnet still in place. Finally the second magnet was taken away and a return from the microsphere to its original orientation was observed (FIG. 29j-l). The images in FIG. 29 were selected from a series of 50 images taken at a 1.2 second interval recording the movement of the microsphere. In some images, the arrow was not clearly visible because of a tilt of the original central plane while moving the second magnetic field and due to the fact that a confocal microscope makes optical sections.

In next experiment, the same microsphere as in the previous experiment was used. The microsphere was initially oriented in the magnetic field of the first magnet (FIG. 30a). After having carefully marked the position of this magnet, it was used to rotate the microsphere (FIG. 30b-j) by moving the magnet 360° around the reservoir and finally placing it back in its original position. The microsphere did not return to its original orientation due to a relatively strong interaction between the polymer bead and the glass cover slip. A second magnet was used to loosen the microsphere by quickly moving it once near the reservoir. It was observed that the microsphere returned immediately to its exact original orientation (FIG. 30k-l).

The ferromagnetic-coated particles could be easily magnetized using a strong magnet. The microspheres could be oriented in an external magnetic field. The orientation of the microspheres in a certain external magnetic field was exactly reproducible after random movement of the spheres when the initial field was applied again. No difference in orientation could be observed within pixel accuracy (0.7 μm/pixel).

13. Example of the use of spherical microcarriers with a single axis of symmetry for identification purposes i.e. encoding and reading in a flow cell.

The necessity of an orientation and a positioning for identification purposes will be elucidated hereunder. The code on said spherical microcarrier is written along the symmetry axis, whereby the code is encoded (written) or identified (read) by means of a high spatial resolution light source, more in particular by using fluorescence bleaching.

Spherical microcarriers are oriented with their symmetry axis along the flow. The laser beam for fluorescence bleaching has a stationary position in the confocal microscope, and the code on said microcarrier is written along the symmetry axis. The flow itself served as the scanning motion along the symmetry axis. A code written as described above (along the symmetry axis), may be read by a laser beam having a stationary position. FIGS. 31a, 31b, 31i, 31j represent schematic field of views of a microcarrier flowing in front of a microscope objective. FIGS. 31a, 31i show the field of view before the microcarrier arrives into the focused laser beam for reading/writing the code. FIGS. 31b, 31j show the field of view with a microcarrier at the focus position.

In the case of a stationary writing/reading laser beam, and accurate flowing of the microcarrier, the code may be written/read along the axis of symmetry of the microcarrier as illustrated in FIG. 31c. However, in the case where the flow is not sufficiently reproducible with respect to the microscope focus, the code may not be read correctly as illustrated in FIG. 31f, wherein the code is written/read below the axis of symmetry.

As illustrated in FIG. 31d, 31g, an auxiliary laser beam may be used to illuminate the passing microcarrier. In this case, a shadowing effect will be observed, behind the microcarrier, due to partial absorption or reflection of light by said microcarrier. A photodiode consisting of two separated cells (bicell photodetector) is positioned at the opposite side of the flow cell in order to measure the shadowing effect. In FIG. 31d, since the center of the spherical microcarrier crosses the optical axis of the microscope, the same amount of light is collected by the 2 cells, and the bicell photodetector measures a difference signal equal to zero, indicating that the bead passes by at the correct height. In FIG. 31g, since the center of the spherical microcarrier does not cross the optical axis of the microscope, the bicell photodetector measures a difference signal different from zero, indicating that the microcarrier flows too high. Consequently, the use of a photodiode permits the detection of a mispositioning of the microcarriers in the flow and indicates whether said microcarriers flow too high or too low from the optical axis.

This photodiode system may be used to measure the position of the microcarrier before said microcarrier arrives at the focus of the reading/writing the laser beam. In this case, the position error signal generated can be used to adjust the focus of the reading/writing beam. In FIG. 31e, since the position error signal measured is zero, the position of the beam focus was not changed. In FIG. 31h, an error signal is measured in this case, and the beam focus position is moved up. Adjusting the focus of the laser beam can be done be changing the direction of incidence of the writing/reading beam on the microscope objective. An acousto-optic beam deflector can be used as a device that can quickly adapt the direction of the laser beam. The same technique can be used to generate a position error signal for the Z axis, i.e. the optical axis of the microscope. Because there will be only a difference signal at the bicell photodetector, the difference signal can be used to detect the arrival of the microcarreir and can also be used as a trigger for reading and writing.

Obviously, numerous modifications and variations of the present invention are possible in the light of the above teachings. It is therefore to be understood that within the scope of the appended claims, the invention may be practiced otherwise than as specifically described herein.

REFERENCES

*Direct simulation of initial value problems for the motion of solid bodies in a Newtonian Fluid. Part 2. Couette and Poiseuille flows.* J. Feng, H. H. Hu, D. D. Joseph, J. Fluid Mech (1994), vol. 277, pp. 271-301.
*Direct simulation of initial value problems for the motion of solid bodies in a Newtonian Fluid. Part 2. Sedimentation.* J. Feng, H. H. Hu, D. D. Joseph, J. Fluid Mech (1994), vol. 261, pp. 95-134.
*The turning couples on an elliptic particle settling in a vertical channel.* Peter Y. Huang, Jimmy Feng, Daniel D. Joseph, J. Fluid Mech (1994), vol. 271, pp. 1-16.
*Direct Simulation of the motion of solid particles in Couette and Poiseuille flows of viscoelastic fluids.* P.Y. Huang, J. Feng, H. H. Hu, D. D. Joseph, J. Fluid Mech (1997), vol. 343, pp. 73-94.
*Dynamic simulation of the motion of capsules in pipelines.* J. Feng, P. Y. Huang, D. D. Joseph, J. Fluid Mech (1995), vol. 286, pp. 201-227.
*The unsteady motion of solid bodies in creeping flows.* J. Feng, D. D. Joseph, J. Fluid Mech (1995), vol. 303, pp. 83-102.

The invention claimed is:

1. Method for the manipulation for an identification purpose of a microcarrier comprising the steps of:
    (a) an identification purpose step of the microcarrier for the detection of an encoded microcarrier wherein the encoded microcarrier comprises a code written on the microcarrier; and
    (b) a positioning and orientation step prior to or during the identification purpose step wherein said positioning and orientation step comprises:
        (b1) the distribution of the population of microcarriers in a one-layer system; and
        (b2) restricting the rotational movement of the microcarriers, wherein the positioning and orientation step restricts the rotational movement of the microcarrier as a result of the microcarrier having an anistropy in its shape and an electric dipole moment or being magnetic or having a magnetic dipole moment so that rotational movement is restricted upon application of an electrical or magnetic field, and wherein the orientation is done with reference to all three axes unless the code is a known arrangement that is symmetric around one or more axes.

2. Method according to claim 1, wherein the distribution of step (b1) results in a plane configuration having two dimensions (X, V).

3. Method according to claim 1, wherein the distribution of step (b1) results in a line configuration.

4. Method according to claim 1, "wherein said electrical or magnetic field positions or orients a microcarrier having a non-spherical configuration and wherein said electrical or magnetic dipole moment of the microcarrier positions and orients said microcarrier.

5. Method according to claim 4, wherein said electrical or magnetic field positions or orients a microcarrier having an ellipsoidal or cylindrical configuration and wherein said electrical or magnetic dipole moment of the microcarrier positions and orients said microcarrier.

6. Method according to claim 1, wherein the microcarrier is encoded by a code written on the microcarrier by exposing the microcarrier to a spatial resolution light source, said spatial resolution light source being selected from the group consisting of a laser, a lamp, or a source that emits X-rays, a and 13 rays, ion beams, a form of electromagnetic radiation, a laser in combination with a confocal microscope, and a lamp in combination with a confocal microscope.

7. Method for the manipulation for an identification purpose of a microcarrier, comprising the steps of
    (a) providing a microcarrier, wherein the microcarrier is encoded by a code written thereon;
    (b) allowing a target-analyte reaction on or in said microcarrier;
    (c) identifying said microcarrier by manipulating for an identification purpose of said microcarrier comprising the steps of: (c1) an identification purpose step of the microcarrier for the detection of an encoded microcarrier wherein the encoded microcarrier comprises a code written on the microcarrier; and (c2) a positioning and orientation step prior to or during the identification purpose step wherein said positioning and orientation step comprises:
(c2.1) the distribution of the population of microcarriers in a one-layer system; and
(c2.2) restricting the rotational movement of the microcarriers, wherein the microcarrier has an anisotropy in its shape and —an electric dipole moment or being magnetic or having a magnetic dipole moment so that rotational movement is restricted upon application of an electrical or magnetic field, and wherein the orientation is done with reference to all three axes unless the code is a known arrangement that is symmetric around one or more axes.

8. Method according to claim 7, wherein the distribution of step (c 2.1) results in a plane configuration having two dimensions (X, V).

9. Method according to claim 7, wherein the distribution of step (c 2.1) results in a line configuration.

10. Method according to claim 7, wherein the positioning and orientation step results from the non-spherical configuration of the microcarrier.

11. Method according to claim 10, wherein the positioning and orientation step results from the ellipsoidal or cylindrical configuration of the microcarrier.

12. Method according to claim 7, wherein the microcarrier is encoded by a process selected from the group comprising photochroming, chemical etching, material deposition, photobleaching, or exposing said microcarrier to a high spatial resolution light source.

13. Method according to claim 8, wherein the microcarrier is encoded by a process selected from the group comprising photochroming, chemical etching, material deposition, photobleaching, or exposing said microcarrier to a high spatial resolution light source.

14. Method according to claim 1, wherein the microcarrier contains one or more ligands bound to the surface of the microcarrier.

15. Method according to claim 1, wherein the identification step is performed using an optical identification means.

16. Method according to claim 15, wherein said optical identification mean comprises a laser beam, or a transmission microscope or a confocal microscope or a fluorescence microscope.

17. Method for performing a target analyte assay comprising the steps of:
(a) an identification purpose step of the microcarrier for the detection of an encoded microcarrier having a diameter of 0.5 to 300 m, wherein the encoded microcarrier comprises a code written on the microcarrier; and
(b) a positioning and orientation step prior to or during the identification purpose step wherein said positioning and orientation step comprises:
(b1) the distribution of the population of microcarriers in a one-layer system; and
(b2) restricting the rotational movement of the microcarriers, wherein the microcarrier has an anisotropy in its shape and an electric dipole moment or being magnetic or having a magnetic dipole moment so that rotational movement is restricted upon application of an electrical or magnetic field, and wherein the orientation is done with reference to all three axes unless the code is a known arrangement that is symmetric around one or more axes;
(c) allowing a target-analyte reaction on or in said microcarrier; and
(d) identifying said microcarrier.

18. The method of claim 1 wherein the anisotropy in mass distribution results from one region of the microcarrier being more dense so that one side is heavier than the other.

19. The method of claim 1 wherein the anisotropy in mass distribution results from having an asymmetric shape, which is reflected by an asymmetric mass distribution.

20. The method of claim 1, wherein (b2) comprises restricting the rotational movement of the microcarriers, wherein the positioning and orientation step restricts the rotational movement of the microcarrier as a result of the microcarrier having an anisotropy of its shape and at least an anisotropy in mass distribution of the microcarrier.

21. The method of claim 1, wherein (b2) comprises restricting the rotational movement of the microcarriers, wherein the positioning and orientation step restricts the rotational movement of the microcarrier as a result of the microcarrier having an anisotropy of its shape and at least an electric dipole moment or being magnetic or having a magnetic dipole moment so that rotational movement is restricted upon application of an electrical or magnetic field.

* * * * *

UNITED STATES PATENT AND TRADEMARK OFFICE
CERTIFICATE OF CORRECTION

PATENT NO. : 8,735,172 B2
APPLICATION NO. : 12/888187
DATED : May 27, 2014
INVENTOR(S) : Marc Jan René Leblans et al.

It is certified that error appears in the above-identified patent and that said Letters Patent is hereby corrected as shown below:

In the Claims

Column 30, Line 39, in claim 4, replace "claim 1, "wherein" with --claim 1, wherein--.

Column 30, Lines 53/54, in claim 6, "a and 13 rays" should be replaced by --$\alpha$ and $\beta$ rays--.

Column 31, Line 9, in claim 7, replace "and –an electric dipole moment" with --and an electric dipole moment--.

Column 32, Line 5, in claim 17, replace "300 m" with --300 μm--.

Signed and Sealed this
Twenty-third Day of September, 2014

Michelle K. Lee
*Deputy Director of the United States Patent and Trademark Office*